(12) United States Patent
Wels et al.

(10) Patent No.: US 9,918,916 B2
(45) Date of Patent: Mar. 20, 2018

(54) ACTIVE INGREDIENT COMPRISING A MIXTURE OF UNSATURATED DICARBOXYLIC FATTY ACIDS, COMPOSITIONS COMPRISING SAID INGREDIENT AND COSMETIC OR DERMATOLOGICAL USES

(71) Applicants: SEDERMA, Le Perray en Yvelines (FR); CRODA INTERNATIONAL PLC, East Yorkshire (GB)

(72) Inventors: Bas Wels, Houten (NL); Arnaud Fournial, Paris (FR)

(73) Assignees: SEDERMA, Le Perray en Yvelines (FR); CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 15/328,705

(22) PCT Filed: Jul. 23, 2015

(86) PCT No.: PCT/IB2015/055590
§ 371 (c)(1),
(2) Date: Jan. 24, 2017

(87) PCT Pub. No.: WO2016/012973
PCT Pub. Date: Jan. 28, 2016

(65) Prior Publication Data
US 2017/0209350 A1   Jul. 27, 2017

(30) Foreign Application Priority Data
Jul. 25, 2014 (FR) ...................................... 14 57213

(51) Int. Cl.
| A61K 8/362 | (2006.01) |
| A61K 8/67 | (2006.01) |
| A61K 31/201 | (2006.01) |
| A61K 9/00 | (2006.01) |
| A61Q 19/00 | (2006.01) |

(52) U.S. Cl.
CPC .............. *A61K 8/362* (2013.01); *A61K 8/676* (2013.01); *A61K 9/0014* (2013.01); *A61K 31/201* (2013.01); *A61Q 19/00* (2013.01); *A61Q 19/007* (2013.01)

(58) Field of Classification Search
None
See application file for complete search history.

(56) References Cited

U.S. PATENT DOCUMENTS

| 5,695,747 | A | 12/1997 | Forestier |
| 5,795,565 | A | 8/1998 | Eteve |
| 5,891,428 | A | 4/1999 | Greff |
| 6,190,645 | B1 | 2/2001 | SaNogueira |
| 7,354,926 | B2 | 4/2008 | Lintner |
| 7,998,493 | B2 | 8/2011 | Lintner |
| 9,376,366 | B2 | 6/2016 | Allard |
| 2004/0115766 | A1 | 6/2004 | Lintner |
| 2006/0104937 | A1 | 5/2006 | Bailey et al. |
| 2013/0085288 | A1 | 4/2013 | Snead et al. |

FOREIGN PATENT DOCUMENTS

| DE | 10150731 | | 4/2003 |
| DE | 10150732 | | 4/2003 |
| DE | 10233599 | A1 | 2/2004 |
| DE | 10305965 | A1 | 8/2004 |
| DE | 10348631 | A1 | 5/2005 |
| EP | 0518772 | | 12/1992 |
| EP | 0518773 | | 12/1992 |
| EP | 1754513 | | 2/2007 |
| FR | 2902998 | A1 | 1/2008 |
| FR | 2992642 | | 1/2014 |
| JP | 2012176995 | A | 9/2012 |
| WO | 9407837 | | 4/1994 |
| WO | 9705856 | | 2/1997 |
| WO | 02066668 | | 8/2002 |
| WO | 03028692 | A2 | 4/2003 |
| WO | 03032941 | A2 | 4/2003 |
| WO | 03039502 | A1 | 5/2003 |
| WO | 03068141 | | 8/2003 |
| WO | 2004017935 | A1 | 3/2004 |
| WO | 2004024695 | | 3/2004 |
| WO | 2005004891 | A2 | 1/2005 |
| WO | 2005037971 | A1 | 4/2005 |
| WO | 2005048968 | | 6/2005 |
| WO | 2005048969 | A1 | 6/2005 |

(Continued)

OTHER PUBLICATIONS

International Search Report and Written Opinion for International Application No. PCT/IB2015/055590, dated Nov. 11, 2015, 10 pages.
Internatinal Search Report and Written Opinion of the International Searching Authority for International Application No. PCT/GB2015/052135, dated Oct. 7, 2015, 14 pages.
Ohlmann et al., "Isomerizing Olefin Metathesis as a Strategy To Access Defined Distributions of Unsaturated Compounds from Fatty Acids", Journal of the American Chemical Society, vol. 134, No. 33, Aug. 22, 2012, pp. 13716-13729.

(Continued)

*Primary Examiner* — Robert A Wax
*Assistant Examiner* — Melissa Mercier
(74) *Attorney, Agent, or Firm* — RatnerPrestia

(57) ABSTRACT

The ingredient comprises a mixture of unsaturated dicarboxylic acids comprising the Z and E isomers of at least one mono-unsaturated dicarboxylic C12-C24 acid, the concentration of the E isomer being of at least 25% by weight based on the total weight of Z and E isomers. The ingredient can be used to form cosmetic or dermatological compositions, in particular for lightening the skin, improving the clarity and unification of the skin complexion.

27 Claims, No Drawings

(56) References Cited

FOREIGN PATENT DOCUMENTS

| | | |
|---|---|---|
| WO | 2005089707 A1 | 9/2005 |
| WO | 2007029187 | 3/2007 |
| WO | 2007041548 A2 | 4/2007 |
| WO | 2008058680 A1 | 5/2008 |
| WO | 2009104118 A1 | 8/2009 |
| WO | 2010082175 | 7/2010 |
| WO | 2011101258 A2 | 8/2011 |
| WO | 2012061093 | 5/2012 |
| WO | 2012104774 | 8/2012 |
| WO | 2013046137 | 4/2013 |
| WO | 2013105047 | 7/2013 |
| WO | 2013105048 | 7/2013 |
| WO | 2013140144 | 9/2013 |
| WO | 2013140145 | 9/2013 |
| WO | 2014001725 A1 | 1/2014 |
| WO | WO 2014001725 A1 * | 1/2014 ........... C07C 51/353 |

OTHER PUBLICATIONS

Hagiwara et al., "Revisit to (Z)-Civetone Synthesis", Natural Product Communications, Natural Product Inc., vol. 7, No. 7, Jan. 1, 2012, pp. 913-915.

"Pharmaceutical and Cosmetic Use of Dioic Acids", Research Disclosure, Mason Publication, No. 444, Apr. 1, 2011, 6 pgs.

* cited by examiner

SEQUENCE LISTING

<160> NUMBER OF SEQ ID NOS: 19

<210> SEQ ID NO 1
<211> LENGTH: 6
<212> TYPE: PRT
<213> ORGANISM: artificial sequence -continued

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 1

Val Gly Val Ala Pro Gly
1               5

<210> SEQ ID NO 2
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 2

Lys Thr Thr Lys Ser
1               5

<210> SEQ ID NO 3
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 3

Gly Gln Pro Arg
1

<210> SEQ ID NO 4
<211> LENGTH: 4
<212> TYPE: PRT
<213> ORGANISM: artificial sequence
<220> FEATURE:
<223> OTHER INFORMATION: synthetic peptide

<400> SEQUENCE: 4

Arg Ser Arg Lys
1

<210> SEQ ID NO 5
<211> LENGTH: 4
<212> TYPE: PRT
<213> ORGANISM: artificial sequence
<220> FEATURE:
<223> OTHER INFORMATION: synthetic peptide

<400> SEQUENCE: 5

Gly Gln Pro Arg
1

<210> SEQ ID NO 6
<211> LENGTH: 4
<212> TYPE: PRT
<213> ORGANISM: artificial sequence
<220> FEATURE:
<223> OTHER INFORMATION: synthetic peptide
```

```
<400> SEQUENCE: 6

Lys Thr Phe Lys
1

<210> SEQ ID NO 7
<211> LENGTH: 5
<212> TYPE: PRT
<213> ORGANISM: artificial sequence
<220> FEATURE:
<223> OTHER INFORMATION: synthetic peptide

<400> SEQUENCE: 7

Lys Thr Thr Lys Ser
1               5

<210> SEQ ID NO 8
<211> LENGTH: 6
<212> TYPE: PRT
<213> ORGANISM: artificial sequence
<220> FEATURE:
<223> OTHER INFORMATION: Synthetic peptide

<400> SEQUENCE: 8

Gly Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Val Gly Val Ala Pro Gly
1               5

<210> SEQ ID NO 10
<211> LENGTH: 6
<212> TYPE: PRT
<213> ORGANISM: artificial sequence
<220> FEATURE:
<223> OTHER INFORMATION: synthetic peptide

<400> SEQUENCE: 10

His Leu Asp Ile Ile Trp
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is aTryptoline-3-carboxylic acid residu
      (Tpi)

<400> SEQUENCE: 11

His Leu Asp Ile Ile Xaa
1               5

<210> SEQ ID NO 12
<211> LENGTH: 6
```

```
<212> TYPE: PRT
<213> ORGANISM: artificial sequence
<220> FEATURE:
<223> OTHER INFORMATION: Synthetic peptide

<400> SEQUENCE: 12

His Leu Asp Ile Ile Phe
1               5

<210> SEQ ID NO 13
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Amidation by a Palmitoyl chain

<400> SEQUENCE: 13

Tyr Gly Gly Phe Leu
1               5

<210> SEQ ID NO 14
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Amidation by a palmitoyl chain

<400> SEQUENCE: 14

Tyr Gly Gly Phe Pro
1               5

<210> SEQ ID NO 15
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (6)..(6)
<223> OTHER INFORMATION: NH2

<400> SEQUENCE: 15

Glu Glu Met Gln Arg Arg
1               5

<210> SEQ ID NO 16
<211> LENGTH: 5
<212> TYPE: PRT
<213> ORGANISM: artificial sequence
<220> FEATURE:
<223> OTHER INFORMATION: synthetic peptide

<400> SEQUENCE: 16

Tyr Ala Gly Phe Leu
1               5
```

```
<210> SEQ ID NO 17
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation

<400> SEQUENCE: 17

Ala His Ser His
1

<210> SEQ ID NO 18
<211> LENGTH: 6
<212> TYPE: PRT
<213> ORGANISM: artificial sequence
<220> FEATURE:
<223> OTHER INFORMATION: synthetic peptide

<400> SEQUENCE: 18

Ser Ile Lys Val Ala Val
1               5

<210> SEQ ID NO 19
<211> LENGTH: 6
<212> TYPE: PRT
<213> ORGANISM: artificial sequence
<220> FEATURE:
<223> OTHER INFORMATION: synthetic peptide

<400> SEQUENCE: 19

Gly Pro Gln Gly Pro Gln
1               5
```

ACTIVE INGREDIENT COMPRISING A MIXTURE OF UNSATURATED DICARBOXYLIC FATTY ACIDS, COMPOSITIONS COMPRISING SAID INGREDIENT AND COSMETIC OR DERMATOLOGICAL USES

CROSS REFERENCE TO RELATED APPLICATIONS

This application is the National Stage filing of International Appln. No. PCT/IB2015/055590, filed 23 Jul. 2015, and claims priority of French Application No. FR 1457213, filed 25 Jul. 2014, the entire disclosures of which are incorporated herein by reference for all purposes.

TECHNICAL FIELD

The present invention relates to a cosmetic or dermatological active ingredient comprising a mixture of unsaturated dicarboxylic fatty acids, also called dioic acids, a cosmetic or dermatological composition comprising said active ingredient and cosmetic and dermatological uses of said ingredient or composition.

The invention relates more particularly to the treatment of skin and appendages, of human or animal mammalians and especially to a topical treatment.

BACKGROUND ART

An active ingredient based on a mixture of unsaturated dioic acids, comprising the octadec-9-ene-1,18-dicarboxylic acid $(HO(O)C(CH_2)_7CH=CH(CH_2)_7C(O)OH))$ as the major component, hereinafter referred to as the octadecene dioic acid (C18), has already been used in cosmetics, primarily as a skin lightening agent. It has also been described as anti-wrinkles or anti-oxidant. Medical treatments have also been described, including treatment of acne, rosacea, lentigo, dermatosis including hyperpigmentary dermatosis, eczema, impetigo, antimicrobial or deodorant.

All the prior arts refer to the same biotechnological process for producing a mixture of unsaturated dioic acids, comprising the octadecene dioic acid, which is disclosed in the WO94/07837 document. This method involves the biotransformation of a mixture of fatty acids (comprising mainly oleic acid), by a yeast strain, for example of the *Candida* genus, in particular *Candida cloacae*, which transforms the ω-methyl group of the fatty acid into a carboxyl group, thus creating a dioic acid with the same chain length and insaturations as the starting unsaturated acid. A parasitic desaturase activity present in the yeast is also observed in this manufacturing process. The resulting amount of C18 dioic acid with two or more insaturations (that is to say for example the octadecadiene dioic acid or the octadecatriene dioic acid) is increased by comparison with the initial mixture. The manufacturing process provides a mixture containing about 60% of octadecene dioic acid, about 35% of other C18 dioic acids containing two or more insaturations and about 5% of untransformed monocarboxylic acids. This mixture is sold under the trademark Arlatone DIOIC DCA™ by CRODA Company.

The cosmetics and dermatology industries are always in demand for new ingredients, especially, more performing, less expensive in terms of manufacturing and/or acting on a broader range of activities. The present invention aims to meet this demand.

SUMMARY OF THE INVENTION

Accordingly, the present invention provides a cosmetic or dermatological active ingredient comprising a mixture of unsaturated dicarboxylic acids comprising the Z and E isomers of at least one monounsaturated C12-C24 dicarboxylic acid, the concentration of the E isomer being at least 25% by weight based on the total weight of Z and E isomers.

The invention provides the use of an ingredient of the invention as defined above for the manufacture of a cosmetic or dermatological composition.

The invention also provides a cosmetic or dermatological composition comprising an effective amount of a cosmetic or dermatological active ingredient according to the invention and a physiologically acceptable excipient.

The invention further provides an ingredient according to the invention, or a composition according to the invention, for a dermatological treatment.

Furthermore, the invention provides the use of an ingredient of the invention or a composition according to the invention for a non-therapeutical cosmetic treatment of the skin and its appendages. The invention also provides a method of cosmetic or dermatological treatment of the skin and its appendages, comprising the application, in particular topically, to a subject requiring such treatment, of an effective amount of a composition according to the invention.

The invention further provides a mixture of unsaturated dicarboxylic acids comprising the Z and E isomers of at least one monounsaturated dicarboxylic C12-C24 acid, characterized in that the concentration of (i) E isomer is of at least 40% by weight and Z isomer is at most 60% by weight both based on the total weight of Z and E isomers, (ii) saturated dicarboxylic acid is 0.1% to 4% by weight based on the total weight of the composition, and (iii) mono-carboxylic acid is 0.1% to 3% by weight based on the total weight of the mixture.

The mixture of unsaturated dicarboxylic acids of the present invention preferably comprises, consists essentially of, or consists of, at least one dicarboxylic C12-C24 acid, preferably C14 to C22, even more preferably C16 to C20 and especially C18. The mixture of unsaturated dicarboxylic acid includes both the E isomer (or trans-isomer) and the Z isomer (or cis-isomer) of at least one monounsaturated dicarboxylic C12-C24 acid, preferably C14-C22, even more preferably C16 to C20 and especially C18.

The number associated with the C (carbon chain) takes into account the carbons of the carboxylic groups. Thus, the mono-unsaturated dicarboxylic C18 acid refers to a compound having a hydrocarbon chain with 16 carbon atoms, preferably linear, containing one double bond between 2 carbons, with a carboxylic group at both ends of the hydrocarbon chain, e.g.:

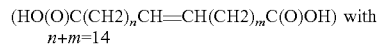

$(HO(O)C(CH2)_nCH=CH(CH2)_mC(O)OH)$ with $n+m=14$

As used herein, the term "unsaturated dicarboxylic acid" includes derivatives thereof, which in the present context comprises esters, salts, and organosulfur compounds in which one or two carboxylic groups are derived. In particular esters and smaller alkyl salts, that is to say C1 to C4, are preferred. Salts, for example of alkali metal, are particularly preferred derivatives because these can be formed spontaneously as a function of the pH of the medium in which the dicarboxylic acids are present.

The position of the double bond between 2 carbons may vary along the hydrocarbon chain. It is preferably in the central part of the chain and more particularly, exactly in the center of that chain. The preferred mono-unsaturated dicarboxylic C18 acid is the octadec-9-ene-1,18-dicarboxylic acid (or octadec-9-ene-1,18-dioic) (HO(O)C(CH$_2$)$_7$CH═CH(CH$_2$)$_7$C(O)OH).

In one embodiment of the invention, the E isomer of the at least one monounsaturated dicarboxylic acid is present in the mixture of dicarboxylic unsaturated acids at a concentration of at least 40%, preferably at least 55%, particularly at least 65%, more particularly at least 75% by weight based on the total weight of Z and E isomers in the mixture. A preferred E isomer is the E isomer of the octadec-9-ene-1,18-dicarboxylic acid.

In one embodiment of the invention, the Z isomer of the at least one monounsaturated dicarboxylic acid is present in the mixture of unsaturated dicarboxylic acids in a concentration of at most 60%, preferably at most 45%, particularly at most 35%, more particularly at most 25% by weight based on the total weight of Z and E isomers in the mixture. A preferred Z isomer is the Z isomer of octadec-9-ene-1,18-dicarboxylic acid (or octadec-9-ene-1,18-dioic acid).

In one embodiment of the invention, the mixture according to the present invention has at least one of the following values: (i) iodine value of 50 to 120 g/100 g, (ii) acid value of 310 to 380 mg KOH/g, and (iii) saponification value of 315 to 380 mg KOH/g.

In one embodiment of the invention, the weight ratio of E/Z isomers in the mixture of unsaturated dicarboxylic acids is suitably from 0.5 to 19:1, preferably from 2 to 10:1, more preferably from 3 to 6:1, particularly from 4 to 5:1, and even more particularly from 4.5 to 4.6:1 based on the total weight of the mixture of isomers Z and E.

In addition to monounsaturated dicarboxylic acids, the composition of unsaturated dicarboxylic acids of the invention may also comprise at least one di-unsaturated dicarboxylic acid and/or at least one tri-unsaturated dicarboxylic acid.

The mixture of unsaturated dicarboxylic acids of the invention suitably comprises (i) at least 65%, preferably at least 80%, particularly at least 90%, more particularly between 95% and 99.5%, and in particular between 96% and 98% by weight of at least one monounsaturated dicarboxylic C12-C24 acid, preferably C14-C22, especially C16-C20, and more especially C18; (ii) less than 25%, preferably less than 15%, even more preferably less than 8%, particularly between 0.4% and 4% and more particularly between 1.7% and 3.4% by weight of at least one di-unsaturated dicarboxylic C12 to C24 acid, preferably C14 to C22, especially C16 to C20, and more especially C18; and/or (iii) less than 10%, preferably less than 5%, even more preferably less than 2%, particularly between 0.1% and 1% and more particularly between 0.3% and 0.6% by weight of at least one tri-unsaturated dicarboxylic C12 to C24 acid, preferably C14 to C22, especially C16 to C20, especially C18, all based on the total weight of unsaturated dicarboxylic acids in the mixture.

In one embodiment of the invention, the combined concentration of the at least one di-unsaturated dicarboxylic acid, and of the at least one tri-unsaturated dicarboxylic acid in the mixture of unsaturated dicarboxylic acids of the invention is less than 35%, preferably less than 20%, even more preferably less than 10%, particularly between 0.5% and 5% and more particularly between 2% and 4% by weight, based on the total weight of unsaturated dicarboxylic acids in the mixture.

In another embodiment of the invention, the mixture is substantially free from di-unsaturated and/or tri-unsaturated dicarboxylic C12 to C24 acid.

The mixture of unsaturated dicarboxylic acids of the invention suitably comprises less than 10%, preferably less than 6%, even more preferably between 0.1% and 4%, particularly between 1% and 3%, and more particularly between 1.5% and 2.5% by weight of at least one saturated dicarboxylic C12 to C24 acid, preferably C14 to C22, especially C16-C20, especially C18, based on the total weight of the mixture.

The mixture of unsaturated dicarboxylic acids of the invention suitably comprises less than 5%, preferably less than 3%, even more preferably between 0.01% and 1%, particularly between 0.15% and 0, 5%, more particularly between 0.25% and 0.35% by weight of at least one monocarboxylic C12-C24 acid, preferably C14 to C22, particularly C16 to C20, more particularly C18, based on the total weight of the mixture.

The mixture of unsaturated dicarboxylic acids of the invention suitably has an iodine value (as measured and described below) of less than 200, preferably between 30 and 150, more preferably from 50 to 120, especially 60 to 100, more particularly between 70 and 90 iodine g/100 g. The iodine value doses the insaturations.

The mixture of unsaturated dicarboxylic acids of the invention suitably has an acid value (as measured and described below) of less than 450, preferably between 290 and 400, more preferably from 310 to 380, especially from 330 to 360, and more particularly between 340 and 350 KOH mg/g. The acid value doses the free acid functions.

The mixture of unsaturated dicarboxylic acids of the invention suitably has a saponification value (measured and described below) of less than 450, preferably between 295 and 400, more preferably from 315 to 380, particularly from 335 to 360, and more particularly between 345 and 350 KOH mg/g. The saponification doses the free and esterified acid functions.

In one embodiment of the invention the active ingredient of the invention further comprises at least one antioxidant or free radical scavenger to protect the mixture against oxidation and allow long-term storage without significant degradation. The active ingredient of the invention preferably comprises from about 0.001% to 5%, more preferably from 0.01% to 1% by weight of at least one anti-oxidant or radical scavenger, based on the total weight of the ingredient.

The at least one anti-oxidant/radical scavenger may be added to the active ingredient of the invention during its manufacture and/or added to the cosmetic or dermatological composition during its manufacture.

Suitable antioxidants/radical scavengers, selected from the group consisting of ascorbic acid (vitamin C) and its salts, ascorbyl fatty esters such as ascorbyl palmitate, derivatives of ascorbic acid (i.e. magnesium ascorbyl phosphate, sodium ascorbyl phosphate, ascorbyl sorbate), tocopherol (vitamin E), tocopherol sorbate, tocopheryl acetate, other esters of tocopherol, tocotrienols associated or not with tocopherols, bisabolol, linoleic acid, 6-hydroxy-2,5,7,8-tetramethylchroman-2-carboxylic acid (commercially available under the name Trolox™), gallic acid and its alkyl esters, especially propyl gallate, uric acid, its salts and alkyl esters, sorbic acid and its salts; lipoic acid, amines (e.g. N,N-diethylhydroxylamine, amino-guanidine), sulfhydryl compounds (e.g. glutathione), dihydroxy fumaric acid and its salts, lysine pidolate, amino acids, silymarin, lysine, 1-methionine, proline, olive extracts, tea extracts, polyphenols such as proanthocyanidins from pine bark, carotenoids, curcumin compounds such as tetrahydrocurcumin, OCTA (L-2-oxo-4-thiazolidine carboxylic acid), melanin, rosemary extracts, extracts of skin or grapes of grapefruit, pentaerythrityl tetra-di-t-butyl hydroxyhydrocinnamate, butylated hydroxytoluene (BHT) and butylated hydroxyanisole (BHA), the orizanol, ethyl hexyl ferulate, may be used.

Preferably anti-oxidants/radical scavengers for use according to the invention are selected from tocopherol (such as Coviox™ T70), bisabolol, tocopherol acetate, ascorbyl palmitate, butylated hydroxytoluene (BHT) and pentaerythrityl tetra-di-t-butyl hydroxyhydrocinnamate and mixtures thereof.

The inventors have shown that, very surprisingly, such an active ingredient has improved efficacy on cosmetic and dermatological treatments compared with an active ingredient of the prior art that do not exhibit at least 25% of E isomer, in particular with respect to a mixture of unsaturated dioic acids obtained by biotransformation. Comparative results are given below in the detailed description.

The biotechnological process of the prior art described above applied to oleic acid provides the Z isomer of the octadecene dioic acid, the oleic acid of natural origin consisting of over than 99% of the Z isomer (cis).

The E isomer can be obtained in particular by another process, known as metathesis, in particular self-metathesis, which implements the rearrangement of double bonds according to the below scheme in the presence of a specific ruthenium catalyst:

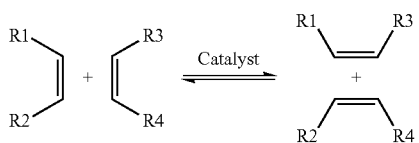

For the synthesis of octadecene dioic acid of the invention, two molecules of methyl oleate can be recombined by metathesis to give the corresponding diester (dimethyl 1.18-octadecen-9-dioate and 9-octadecene), as shown in the below scheme:

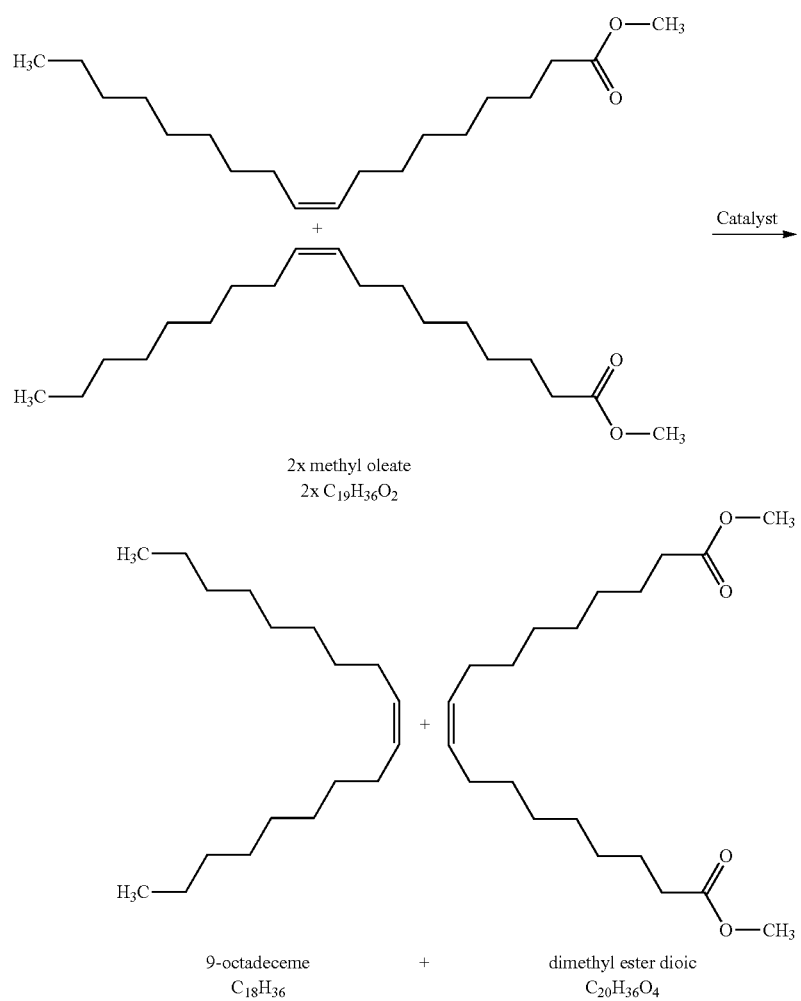

The two products thus formed and the unreacted substrate are then separated by distillation and finally a step of hydrolyzing of the dimethyl ester dioic leads to octadecenedioic acid. Oleic acid can also be used as the starting product.

The metathesis reaction is described in the international applications WO2013/140144 and WO2013/140145. A choice of catalyst/catalyst activator is described in the patent applications WO2013/140144 and WO2013/140145. The E isomer of the octadecene dioic acid can be produced via this metathesis route.

The specific ratio of the isomers E with regard to the Z isomers required in the composition of at least one unsaturated dicarboxylic acid according to the present invention can be obtained by combining a mixture resulting from the metathesis (majority of E isomers of monounsaturated dicarboxylic acid(s) with a mixture obtained from the biotransformation by fermentation (Z acid isomers of monounsaturated dicarboxylic acid(s)).

The ingredient according to the invention can advantageously be used for a non-therapeutic cosmetic treatment of the skin and its appendages, in particular a topical treatment. The aim of such cosmetic treatment is to improve the general condition of skin and its appendages. In a cosmetic composition, the ingredient will generally be used at a concentration between 0.01% and 20%, preferably from 0.05% to 10%, particularly from 0.1% to 5% and especially around 1%, 2% and 4% by weight relative to the total weight of composition.

More particularly, the cosmetic treatment of the invention may be chosen especially from treatments:
To reduce the production of melanin in the skin,
To lighten the skin and its appendages,
To attenuate skin spots,
To homogenize skin color,
To hydrate,
To fight against cutaneous dryness,
To protect and/or reinforce the skin barrier,
For stimulating the synthesis of at least one of the molecules of the dermal extracellular matrix,
Antioxidant
Anti-wrinkles,
Slimming,
To improve the mechanical properties of the skin: firmness and/or elasticity and/or flexibility,
For a lipofiling by promoting the expansion and/or the formation of subcutaneous adipose tissue in order to improve and/or embellish any part of the body with a lipid deficiency,
Anti-aging,
Of oily skin,
Of acne-prone skin (prevention and treatment),
Anti-dandruff,
Acting on hair and nails growth,
Peeling,
Anti-solar radiations,
Deodorant,
Anti-seborrheic,
Antiglycation,
Promoting re-epithelialization and/or regeneration of the skin or the lips, and of the contour of the hair root or nails, and/or
To improve comfort of the skin affected by cold, UV or mechanical frictions.

A particularly interesting use of the invention, as shown by in vivo tests given below in the description is the lightening treatment of skin of V and/or VI phenotypes, and more particularly phenotypes VI (black skins).

According to the invention, the active ingredient can also be used for a dermatological treatment, in particular a topical anti-bacterial, anti-microbial, anti-inflammatory, anti-acne, against pimples, rosacea, lentigo, including hyperpigmentary dermatosis, eczema or impetigo treatments.

The invention ingredient can advantageously be incorporated in a cosmetic composition as a lightening active ingredient acting in a multifactor way. This ingredient lightens skin in reducing melanogenesis and tyrosinase activity in melanocytes, and melanosome transfer from melanocytes to keratinocytes. Moreover in reducing oxidative and inflammatory process, the invention ingredient reduces the amount of pigmented by-products. Finally, the invention mixture protects skin against UV damages, in reinforcing barrier function in the skin and then playing a role of natural sunscreen.

Other cosmetic and therapeutic applications can be envisaged.

According to other advantageous characteristics, the active ingredient of the invention can be used in combination with one or more additional or complementary active ingredients, offering advantageously the possibility of a wider range of cosmetic properties. The combined effects can advantageously be additive or have a synergistic effect.

The additional active ingredients may for example be selected from lightening, anti-redness, against spots, calming, sunscreens, moisturizing, humectant, exfoliating, smoothing, toning, anti-aging, anti-fine lines and wrinkles, improving mechanical and elastic properties, complexion, detoxifying, anti-hair regrowth, anti-acne, acting on sebum secretion, matting, unifying, anti-inflammatory, anti-oxidant/radical scavengers (including those described above for use in the ingredient according to the invention), anti-glycation, anti-dandruff, eye contours (dark circles and under eye bags), promoting blood circulation, peptides and vitamins active ingredients, etc. These active ingredients may be obtained from plant materials, such as plant extracts or plant cell culture or fermentation products.

More specifically, the composition according to the invention may be combined with at least one of compounds selected from compounds of the vitamin B3, compounds such as niacinamide or tocopherol, retinoid compounds such as retinol, hexamidine, α-lipoic acid, resveratrol or DHEA, peptides, in particular N-acetyl-Tyr-Arg-O-hexadecyl ester, Pal-VGVAPG (SEQ ID NO: 1), Pal-KTTKS (SEQ ID NO: 2), Pal-GHK, Pal-KMO2K and Pal-GQPR (SEQ ID NO: 3), which are widely used active ingredients in topical cosmetic or dermopharmaceutical compositions.

The CTFA (<<International Cosmetic Ingredient Dictionary & Handbook>> (15th Ed. 2014) published by << the Personal Care Products council>>, ex-<< the Cosmetic, Toiletry, and Fragrance Association, Inc.>>, Washington, D.C.), describes a non-limited wide variety of cosmetic and pharmaceutical ingredients commonly used in the skin care industry, which are suitable for use as additional ingredients in the compositions according to the present invention.

Further additional skin care actives that are particularly useful can be found in the commercial literature of Sederma and on the website www.sederma.com.

The following commercial actives can also be mentioned, as examples: betaine, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (commercial name for the acetyl hexapeptide-3 of Lipotec), spilanthol or an extract of *Acmella oleracea* known under the commercial name Gatuline Expression™, an extract of *Boswellia serrata* known under the commercial name Boswellin™, Deepaline PVB™ (Seppic), Syn-AKE™ (Pentapharm), Ameliox™, Bioxilift™ (Silab), PhytoCellTec™ Argan (Mibelle), Papilactyl D™ (Silab), Preventhelia™ (Lipotec), Subliskin™ (Sederma), Venuceane™ (Sederma), Moist 24™ (Sederma), Vegesome Moist 24™ (Sederma), Essenskin™ (Sederma), Juvinity™ (Sederma), Revidrat™ (Sederma), Resistem™

(Sederma), Chronodyn™ (Sederma), Kombuchka™ (Sederma), Chromocare™ (Sederma), Calmosensine™ (Sederma), Glycokin factor S™ (Sederma), Biobustyl™ (Sederma), Idealift™ (Sederma), Ceramide 2™, Ceramide A2™ et Ceramide HO3™ (Sederma), Legance™ (Sederma), Intenslim™ (Sederma), Prodizia™ (Sederma), Beautifeye™ (Sederma), NG-shea butter unsaponifiables (natural grade)(Sederma), Zingerslim™ (Sederma), Meiritage™ (Sederma), Senestem™ (Sederma), Sebuless™ (Sederma), Majestem™ (Sederma), Apiscalp™ (Sederma), Rubistem™ (Sederma) or mixture thereof.

Among other plant extracts which can be combined with the composition of the invention, there may more particularly be mentioned extracts of Ivy, in particular English Ivy (*Hedera Helix*), of *Bupleurum chinensis*, of *Bupleurum Falcatum*, of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria L*), of big-flowered Jarva tea (*Orthosiphon Staminicus Benth*), of algae (*Fucus Vesiculosus*), of birch (*Betula alba*), of green tea, of cola nuts (*Cola Nipida*), of horse-chestnut, of bamboo, of *Centella asiatica*, of heather, of fucus, of willow, of mouse-ear, of escine, of cangzhu, of *chrysanthellum indicum*, of the plants of the *Armeniacea* genus, *Atractylodis Platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Siegesbeckia*, in particular *Siegesbeckia orientalis*, vegetable extracts of the family of *Ericaceae*, in particular bilberry extracts (*Vaccinium angustifollium*) or *Arctostaphylos uva ursi, aloe vera*, plant containing sterols (e.g., phytosterol), Manjistha (extracted from plants of the genus *Rubia*, particularly *Rubia Cordifolia*), and Guggal (extracted from plants of the genus *Commiphora*, particularly *Commiphora Mukul*), kola extract, chamomile, red clover extract, *Piper methysticum* extract (Kava Kava™ from SEDERMA), Bacopa monieri extract (Bacocalmine™ from SEDERMA) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa Hirudinea*, of *Chaparral Sorghum*, of sun flower extract, of *Enantia chlorantha*, of *Mitracarpe* of *Spermacocea* genus, of *Buchu barosma*, of *Lawsonia inermis* L., of *Adiantium Capillus-Veneris* L., of *Chelidonium majus*, of Luffa *cylindrica*, of Japanese Mandarin (*Citrus reticulata Blanco* var. *unshiu*), of *Camelia sinensis*, of *Imperata cylindrica*, of *Glaucium Flavum*, of *Cupressus Sempervirens*, of *Polygonatum multiflorum*, of *lovelyly hemsleya*, of *Sambucus Nigra*, of *Phaseolus lunatus*, of *Centaurium*, of *Macrocystis Pyrifera*, of *Turnera Diffusa*, of *Anemarrhena asphodeloides*, of *Portulaca pilosa*, of *Humulus lupulus*, of *Coffea Arabica*, of *Ilex Paraguariensis*, or of *Globularia Cordifolia*, of *Albizzia julibrissin*, of *Oxydendron arboretum*, of *Zingimber Zerumbet Smith*, of *Astragalus membranaceus*, of *Atractylodes macrocephalae*, of *Plantago lanceolata*, of *Leontopodium alpinum*, of *Mirabilis jalapa* or of *Apium graveolens*.

The compositions of the present invention may include peptides, including, without limitation, the di-, tri-, tetra-, penta- and hexapeptides and their derivatives. According to a particular embodiment, the concentration of the additional peptide, in the composition, ranges from $1 \times 10^{-7}$% and 20%, preferably from $1 \times 10^{-6}$% and 10%, preferably between $1 \times 10^{-5}$% and 5% by weight.

According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (beta-AH), YR, VW, NF, DF, KT, KC, CK, KP, KK or TT. Suitable tripeptides for use herein include, but are not limited to RKR, HGG, GHK, GKH, GGH, GHG, KFK, GKH, KPK, KMOK, KMO2K or KAvaK. Suitable tetrapeptides for use herein include but are not limited to RSRK (SEQ ID NO: 4), GQPR (SEQ ID NO: 5) or KTFK (SEQ ID NO: 6). Suitable pentapeptides include, but are not limited to KTTKS (SEQ ID NO: 7). Suitable hexapeptides include but are not limited to GKTTKS (SEQ ID NO: 8) and VGVAPG (SEQ ID NO: 9).

Other suitable peptides for use herein include, but are not limited to: lipophilic derivatives of peptides, preferably palmitoyl derivatives, and metal complexes as aforementioned (e.g. copper complex of the tripeptide HGG). Preferred dipeptide include for example N-Palmitoyl-beta-Ala-His, N-Acetyl-Tyr-Arg-hexadecylester (Calmosensine™, Idealift™ from Sederma). Preferred tripeptide derivatives include for example N-Palmitoyl-Gly-Lys-His, and Pal-Gly-His-Ly, (Pal-GKH and Pal-GHK from Sederma), the copper derivative of HGG (Lamin™ from Sigma), Lipospondin (N-Elaidoyl-KFK) and its analogs of conservative substitution, N-Acetyl-RKR-NH2 (Peptide CK+), N-Biot-GHK (from Sederma), Pal-KMO2K (Matrixyl Synthe6™ from Sederma) and derivatives thereof. Suitable tetrapeptide derivatives for use according to the present invention include, but are not limited to, N-Pal-GQPR (SEQ ID NO: 3) (from Sederma), suitable pentapeptide derivatives for use herein include, but are not limited to, Pal-KTTKS (SEQ ID NO: 2) (available as Matrixyl™ from Sederma), Pal-YG-GFL (SEQ ID NO: 10) or Pal-YGGFP (SEQ ID NO: 11) or mixtures thereof. Suitable hexapeptide derivatives for use herein include, but are not limited to, Pal-VGVAPG (SEQ ID NO: 1), HLDIIW (SEQ ID NO: 12), HKDIITpi (SEQ ID NO: 13), Tpi being the Tryptoline-3-carboxylic acid residue, or HLDIIF (SEQ ID NO: 14), or Pal-, and derivatives thereof. The mixture of Pal-GHK and Pal-GQPR (SEQ ID NO: 3) (Matrixyl™ 3000, Sederma) can also be mentioned.

The preferred compositions commercially available containing a tripeptide or a derivative include Biopeptide-CL™, Maxilip™, Biobustyl™, Procapil™ and Matrixyl™ synthe'6™ of Sederma. The compositions commercially available preferred sources of tetrapeptides include Rigin™, Eyeliss™, Matrixyl™ Reloaded and Matrixyl 3000™ which contain between 50 and 500 ppm of Pal-GQPR (SEQ ID NO: 3) and an excipient, proposed by Sederma.

The following marketed peptides can be mentioned as well as additional active ingredients:

Vialox™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) marketed by Pentapharm;

Argireline™ (Ac-Glu-Glu-Met-Gln-Arg-Arg-NH$_2$ (INCI name=Acetyl hexapeptide-3) (SEQ ID NO: 15), Leuphasyl™ (Tyr-D-Ala-Gly-Phe-Leu) (SEQ ID NO: 16), Aldenine™ (Gly-His-Lys), Trylagen™ (INCI name=*Pseudoalteromonas* Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-(3-Ala-His-Ser-His)(SEQ ID NO: 17), Serilesine™ (Ser-Ile-Lys-Val-Ala-Val) (SEQ ID No 18) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;

Collaxyl™ (Gly-Pro-Gln-Gly-Pro-Gln (SEQ ID No 19)) or Quintescine™ (Cys-Gly) marketed by Vincience;

Cytokinol™ LS (casein hydrolysate) marketed by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) marketed by l'Institut Européen de Biologie Cellulaire;

Neutrazen™ (Pal-His-D-Phe-Arg-NH$_2$) marketed by Innovations; or

BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by Infinitec Activos.

According to other features of the invention, in a cosmetic or dermatological composition, the ingredient of the invention may be combined with a sunscreen, preferably having the widest possible protection spectrum, filtering UVA and UVB, but also capable of filtering more specifically IR, close-UV and/or HEV (high energy visible) radiations.

Suitable sunscreens can be organic or inorganic. A wide variety of organic and inorganic usual sunscreens can be used in the context of the present invention. The exact amount of filter varies depending on the sunscreen chosen and the desired sun protection factor (SPF).

The following examples of organic filters can be cited:

para-aminobenzoic acid (PABA) derivatives: ethyl dihydroxypropyl PABA, ethylhexyl dimethyl PABA marketed in particular under the commercial name Escalol 507™ by ISP, glyceryl PABA, PEG-25 PABA marketed under the commercial name Uvinul P25™ by BASF;

salicylic derivatives: homosalate marketed under the commercial name Eusolex HMS™ by Rona/EM Industries, ethylhexyl salicylate marketed under the commercial name Neo Heliopan OS™ by Haarmann and Reimer, dipropyleneglycol salicylate marketed under the commercial name Dipsal™ by Scher, TEA salicylate marketed under the commercial name Neo Heliopan TS™ by Haarmann and Reimer;

dibenzoylmethane derivatives: butyl methoxydibenzoylmethane marketed under the commercial name Parsol 1789™ by Hoffmann La Roche and isopropyl dibenzoylmethane;

cinnamic derivatives: ethylhexyl methoxycinnamate marketed under the commercial name Parsol MCX™ by Hoffmann La Roche, isopropyl methoxy cinnamate, isoamyl methoxy cinnamate marketed under the commercial name Neo Heliopan E 1000™ by Haarmann and Reimer, cinoxate, DEA methoxycinnamate, diisopropyl methylcinnamate and glyceryl ethylhexanoate dimethoxycinnamate;

ββ'-diphenylacrylate derivatives: octocrylene marketed in particular under the commercial name Uvinul N539™ by BASF and etocrylene, marketed in particular under the commercial name Uvinul N35™ by BASF;

benzophenone derivatives: benzophenone-1 marketed under the commercial name Uvinul 400™ by BASF, benzophenone-2 marketed under the commercial name Uvinul D50™ by BASF, benzophenone-3 or oxybenzone, marketed under the commercial name Uvinul M40™ by BASF, benzophenone-4 marketed under the commercial name Uvinul MS40™ by BASF, benzophenone-5, benzophenone-6 marketed under the commercial name Helisorb 11™ by Norquay, benzophenone-8 marketed under the commercial name Spectra-Sorb UV-24™ by American Cyanamid, benzophenone-9 marketed under the commercial name Uvinul DS-49™ by BASF and benzophenone-12;

camphor benzylidene derivatives: camphor 3-benzylidene, camphor 4-methylbenzylidene marketed under the commercial name Eusolex 6300™ by Merck, sulfonic acid of camphor benzylidene, benzalkonium methosulfate camphor, terephthalylidene dicamphor sulfonic acid, polyacrylamidomethyl benzylidene camphor;

phenyl benzimidazole derivatives: phenylbenzimidazole sulfonic acid marketed in particular under the commercial name Eusolex 232™ by Merck, benzimidazilate marketed under the commercial name Neo Heliopan AP™ by Haarmann and Reimer;

triazine derivatives: anisotriazine marketed under the commercial name Tinosorb S™ by Ciba Geigy, ethylhexyltriazone marketed in particular under the commercial name Uvinul T150™ by BASF, diethylhexyl butamido triazone marketed under the commercial name Uvasorb HEB™ by Sigma 3V;

phenyl benzotriazole derivatives: drometrizole trisiloxane marketed under the commercial name Silatrizole™ by Rhodia Chimie;

anthranilic derivatives: menthyl anthranilate marketed under the commercial name Neo Heliopan™ by Haarmann and Reimer;

imidazoline derivatives: ethylhexyl dimethoxybenzylidene dioxoimidazoline propionate;

benzalmalonate derivatives: polyorganosiloxane having benzalmalonate functions marketed under the commercial name Parsol SLX™ by Hoffmann La Roche;

dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and 2-naphthol-6,8-disulfonic acids); di-hydroxynaphthoic acid and its salts; o- and p-hydroxybiphenyldisulfonates; coumarine derivatives (7-hydroxy, 7-methyl, 3-phenyl); diazoles (2-acetyl-3-bromoindazole, phenyl benzoxazole, methyl naphthoxazole, various aryl benzothiazoles); quinoline derivatives (2-phenylquinoline salts); uric and violuric acids; tannic acid and derivatives (e.g., hexaethylether); (butyl carbotol) (6-propyl piperonyl) ether; hydroquinone.

Particularly preferred UV sunscreens are chosen from the following compounds: ethylhexyl salicylate, butyl methoxydibenzoylmethane, ethylhexyl methoxycinnamate, octocrylene, phenylbenzimidazole sulfonic acid, terephthalylidene dicamphor sulfonic acid, benzophenone-3, benzophenone-4, benzophenone-5, 4-methylbenzylidene camphor, benzimidazilate, anisotriazine, ethylhexyl triazone, diethylhexyl butamido triazone, methylene bis-benzotriazolyl tetramethylbutylphenol, drometrizole trisiloxane, and mixture thereof. The compositions disclosed in U.S. Pat. No. 6,190,645 patent are also particularly preferred and in particular the sunscreen actives marketed under the commercial name Incroquat-UV-283™ by Croda.

The inorganic filters suitable for the composition according to the invention are in particular nano-pigments (average primary particle size generally between 5 nm and 100 nm, preferably between 10 nm and 50 nm) of coated or not metal oxides such as titanium oxide nano-pigments (amorphous or crystallized in rutile and/or anatase form), of iron, zinc, zirconium, cerium or maganese. Coating agents are moreover alumina and/or aluminum stearate. Such nano-pigments metal dioxides, coated or uncoated, are described in particular in EP0518772 and EP0518773 patent applications.

As a preferred example, the inorganic filter sold by Croda under the commercial range name Solaveil™ can be advantageously mentioned having a broad spectrum of protection, including remarkable regarding UVA and/or UVB. Another preferred inorganic sun filter is the Optisol™ sold by Oxonica or a TiO$_2$ filter modified by manganese (TiO$_2$Mn). The TiO$_2$Mn advantageously provides to the skin, in addition to its filtering action with regard to UV, a unifying, matting and brightening effect, with no white residue.

According to still further features of the invention, in a cosmetic or dermatological composition, the ingredient of the invention may be combined with a known active to protect and/or treat the damages to the skin or its appendages caused by different radiations including the following commercial actives: Cosmedia DC™ from Cognis-Care Chemicals, Helioguard 365™, NanoVit™ and PhytoCellTec™ Solar Vitis from Mibelle AG Cosmetics, Melaneze™ from Dragoco, Vanirea™ from Solabia, Solarine III™, Nucleolys™ and Sun Protection Complex™ from Greentech, Pronalen Sunlife™ from S. Black Ltd., ClC2™ and Antikeuline 6™ from Biotech Marine (Secma Biotechnologies Marines), Parsol SLX™ and Alpaflor Edelweiss™ from DSM Nutritional Products, DN-AGE2™, DN-AGE LS9547™ and Sunactyl LS9610™ from Laboratoires Sdrobiologiques, Uniprotect PT 3™ from Induchem, Maricol S CLR™ from Chemisches Laboratorium Dr. Richter, Illumiscin™ from Indena, Caspaline 14™ and Natriance Antioxidizer™ from Vincience/ISP, Liposhield HEV Melanin™ from Lipo Chemicals, Fruit Vinegar™ from Provital SA, IBR-TCLC 0701™ from IBR, Venuceane™ from Sederma and Muciliance Fruit™ from Soliance.

Furthermore, it is particularly advantageous, that the compositions according to the present invention comprise in addition at least one skin lightening and/or whitening active. The compositions then comprise preferably from 0.01% to 20%, preferably from 0.02% to 10%, and particularly from 0.05% to 5% by weight of at least one skin lightening and/or whitening active relative to the total weight of the composition.

The skin lightening and/or whitening agents may act by different mechanisms: they can be inhibitors of tyrosinase activity, tyrosinase suppressors, tyrosinase competitors, reducers of the formation of melanin, or anti-oxidants. These agents have with the active ingredient of the invention a complementary effect, additive or synergistic.

Such agents include those known by those skilled in the art, for example vitamin C and ascorbic acid derivatives (ethyl ascorbic acid, ascorbyl glucoside, magnesium ascorbyl phosphate, sodium ascorbyl phosphate, disodium ascorbyl sulfate, ascorbyl tetraisopalmitate), niacinamide, licorice root extract (*Glycyrrhiza glabra* (licorice) root extract), arbutin, kojic acid, alpha-bisabolol, ellagic acid, linoleic acid, m-tranexamic, hydroquinone, corticosteroids, mercury, aminophenol derivatives, N-cholesteryloxycarbonyl-para-aminophenol and N-ethyloxycarbonyl-para-aminophenol; iminophenol derivatives, L-2-oxothiazolidine-4-carboxylic acid or procysteine, and its salts and esters, and extracts (ie extract of mulberry (Broussonetia extract), licorice (Lycoris aurea extract), placenta, skullcap extract, licorice soluble oil (i.e. proposed by Maruzen), extracts of camomile (i.e. proposed by Kao)), t-AMCHA, 4MSK (proposed by Shiseido), adenosine monophosphate disodium (APM offered by Otsuka), rucinol (Pola).

The skin lightening and/or whitening agents that can be used in the present invention include combinations with lightening agents called Melaclear™, Etioline™, Melaslow™, Wonderlight™, Inexwhite™, et Lumiskin™/Lumisphere™ provided by Sederma.

Other skin lightening and/or whitening agents that can be used in the context of the present invention include the products sold under the names: NAB Asefetida Extract™ (Arch Chemicals, Inc.), Actiwhite™ (BASF), Tego Pep 4 Even™ (Evonik), Synerlight 2™ (Gatefossé), Clerilys™ (Greentech), AA2G™ (Hayashibara), Uninontan U 34™ (Induchem), B-White™, Tyrostat™, and Melanostatine 5™ (Lucas Meyer-Unipex), NanoWhite™ (Mibelle AG Cosmetics), Melavoid™ (Provital SA), Cellactive White™ (Rahn GmbH), Emblica™ (Rona), Azeloglicina™ (Sinerga), Sepicalm VG™ and Sepiwhite MSH™ (Seppic), Whitonyl™ (Silab), Axolight™ (Soliance), and Symwhite 377™ (Symrise).

The preferred skin lightening and/or whitening agents are the vitamine C and the ascorbic acid derivatives (ethyle ascorbic acid, ascorbyle glucoside, magnesium ascorbyl phosphate, sodium ascorbyl phosphate, disodium ascorbyl sulfate, ascorbyl tetraisopalmitate), niacinamide, extract of licorice root (*Glycyrrhiza glabra* (licorice) root extract), and arbutine.

For a scalp treatment will be preferably used in addition to or reinforcement of activity:

An anti-dandruff active acting as an antifungal, such as zinc pyrithione, ketoconazole, climbazole, piroctone olamine or selenium disulphide;

A moisturizing agent such as DuraQuench™ (Croda);

An active rebalancing skin microflora as HAIRSPA™ (Sederma);

A soothing active as PACIFEEL™ (Sederma); and/or

Cosmetic active to prevent hair loss and stimulate their growth as CAPIGENE™ (Sederma), CAPILECTINE™ (Sederma), PROCAPIL™ (Sederma), or to reinforce the structure of damaged hair as CERAMIDE A2™ (Sederma), HELIOGENOL™ (Sederma), or to smooth the hair as FRUIT BIO™ (Sederma).

Preparation of the Cosmetic or Dermatological Compositions

"Physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hair and hairs), scalp and skin of mammals, particularly human, compositions which may be ingested, or injected into the skin, without risk of toxicity, incompatibility, instability, allergic response, and others.

This "physiologically acceptable medium" forms what is commonly called the excipient of the composition.

For the use according to the invention, the effective amount of the active ingredient in the composition, that is to say its dosage, depends on various factors, such as the age, the condition of the skin of the patient, etc. An effective amount means a non-toxic amount enough to achieve the desired effect.

For the use according to the invention, the ingredient according to the invention, to be present in an effective amount, is generally present in an amount ranging from 0.01 and 20%, preferably from 0.05% to 10%, particularly from 0.1% to 5%, and in particular about 1%, 2%, 3% and 4% in weight with regard to the total weight of the composition. The one skilled in the art is capable of adjusting the active content depending on the specific destination and the desired effect.

All percentages and ratios used herein are by weight of the total composition and all measurements are made at 25° C. unless it is otherwise specified.

The choice of the excipient of the composition is made according to the constraints in link with the ingredient itself (its stability, solubility, etc.), and if necessary according to the galenic form envisaged afterwards for the composition.

The active ingredient of the invention can be incorporated in a composition by means of usual physiologically acceptable solubilizers, such as for example: alkaline water, ethanol, propanol, isopropanol, propylene glycol, butylene glycol, 1,3 propane diol, or polyethylene glycol or any combination thereof.

According to one form of realization, the composition according to the invention is in a form of an emulsion (or dispersion), such as an oil-in-water or water-in-oil emulsion.

The oil phase of the emulsion will preferably be an emollient oil of the type used in cosmetics. This type of material is preferably liquid at room temperature. But a solid material at room temperature (wax type) can also be used, which will be hot incorporated into the final composition.

Suitable liquid oils in which the active ingredient according to the invention can be heat dissolve include non-polar oils such as mineral or paraffin, or medium polarity oils, such as esterified vegetable oils (e.g. jojoba oil), triglyceride based vegetable or animal oils (caprylic/capric triglycerides for example), esterified synthetic oils such as isopropyl palmitate, etherified oils like dicaprylether, octyldodecanol or silicones oils such as dimethicone oil, cyclomethicone, or silicone oils having polyoxyalkylene side chains to improve their hydrophilicity, or finally highly polar oils such as propoxylated fatty alcohols.

A powder support can also be used.

The compositions adapted to the present invention are generally prepared by conventional methods well known to one skilled in the art for making topical or oral compositions and compositions for injection. Such methods may involve a mixture of ingredients in one or more steps to obtain a uniform state, with or without heating, cooling, etc.

All galenic forms that can contain the composition according to the invention can be used, i.e., creams, lotions, milk or cream ointments, gels, emulsions, dispersions, solutions, suspensions, cleansers, foundations, anhydrous preparation (sticks for example lip balm, body and bath oils), shower and bath gels, shampoos and hair care lotions, milks or creams for skin and hair cares, cleansing lotions or milks, sunscreen lotions, milks or creams, pre-shave, shaving or after-shave creams, foams, gels or lotions, make-up, lipsticks, mascaras or nail varnishes, skin "essences," serums, adhesive or absorbent materials, transdermal patches, emollient powders, lotions, milks or creams, sprays, oils for the body and the bath, foundation tint bases, pomade, emulsion, colloid, compact or solid suspension, pencil, sprayable or brossable formulation, blush, red, eyeliner, lip liner, lip gloss, facial or body powder, styling foams or gels, nail conditioner, lip balms, skin conditioners, moisturizers, hair sprays, soaps, exfoliation agent, astringents, depilatories, permanent waving solutions, antidandruff formulations, anti-sweat and antiperspirant compositions, such as sticks, roll-on deodorant, deodorizing agent, nose sprays, etc. These compositions can also be presented in the form of lipsticks intended to apply color or to protect the lips from cracking, or of make-up products for the eyes or tints and tint bases for the face. Compositions in accordance with the invention include cosmetics, personal care products and pharmaceutical preparations. A composition in the form of foam or in the form of compositions for aerosol also including a propellant agent under pressure can be envisaged.

Compositions according to the invention may also be for orodental use, for example, toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

The active ingredient within the scope of the present invention may be used in the form of solution, dispersion, emulsion, paste, or powder, individually or as a premix or in vehicles individually or as a premix in vectors such as macro-, micro-, or nano-capsules, macro-, micro- or, nano-spheres, liposomes, oleosomes or chylomicrons, macro-, micro-, or nanoparticles or macro-, micro- or nano-sponges, micro- or nano-emulsions or adsorbed on organic polymer powders, talcs, bentonites, spores or exines, and other inorganic or organic supports.

The encapsulation of the acid mixture or ingredient of the invention can be in particular envisaged in microcapsules of polymethylmethacrylate and manganese modified titanium dioxide ($TiO_2Mn$).

The composition of the present invention may be used in any form whatsoever, in a form bound to or incorporated in or absorbed in or adsorbed on macro-, micro-, and nano-particles, or macro-, micro-, and nano-capsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

Cosmetic Treatment Method

The invention also provides a cosmetic or dermopharmaceutical treatment method of the skin and its appendages comprising the application, in particular topically, to the skin of a subject in need thereof of an effective amount of a composition according to the invention.

<<Topical treatment>> means according to the invention, an application that is intended to act where it is applied: skin, mucosa and/or appendages.

Improvements of the appearance and general state of sensitive skin can be obtained by topical application on a regular basis, for example daily or bi-daily.

The practitioner will appreciate the dermopharmaceutical or cosmetic treatment that will include a preparation comprising the ingredient according to the invention, this treatment being achieved for example by applying topically the preparation described in the present invention, according to a method usually used to apply such a composition. The topical preparation is preferably applied once a day for a period of at least one week, but it can be applied for periods of 2, 4, 8 or 12 weeks.

Preferably, the topical composition is applied to the face and neck, but can be applied to any skin part requiring a treatment, where the composition remains on the skin area to be treated, and preferably is not removed or flushed from the skin.

For example, for a face cosmetic treatment, the European Cosmetics Directive has set a standard amount for applying a cream of 2.72 mg/cm2/day/person and for a body lotion of 0.5 mg/cm2/day/person.

It is also to be understood that, as used herein, the terms treating and treatment include and encompass in particular the improvement, reduction, protection, progress, relief, and/or elimination of skin, appendages and mucous membranes in need thereof.

The compositions of the present invention and the methods can be used for the treatment of dermatological conditions of skin in numerous areas of skin, including without limitation face, forehead, lips, neck, chest, breasts, arms, hands, body, legs, knees, feet, back, buttocks, or abdomen or else.

One of the major advantages of the present invention resides in the ability whenever necessary or desirable to be able to apply local selective "gentle" treatments through this topical, non-invasive method of application. An application can be realised very locally using a syringe or micro-canula.

It is also possible, however, to consider a composition containing the ingredient according to the invention intended to be injected subcutaneously.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing the ingredient of the invention, and in a second compartment a composition containing another active ingredient and/or excipient, the compositions contained in the said first and second compartments in this case being considered to be a combination composition for simultaneous, separate or stepwise use in time, particularly in one of the treatment methods recited above.

More particularly, the method according to the invention can be applied to the following non-therapeutic cosmetic treatments:

For reducing the production of melanin in skin,
For lightening skin and its appendages,
For mitigating cutaneous spots,
For homogenizing skin coloration,
For hydrating,
For fighting dry skin,
For protecting and/or reinforcing cutaneous barrier,
For stimulating at least one of the molecules of the extracellular dermal matrix,
Anti-oxidant,
Anti-wrinkles and fine lines,
Slimming,
For improving mechanical properties of the skin: firming, elasticity and/or flexibility,
For lipofiling by promoting the expansion and/or formation of subcutaneous adipose tissue in order to improve and/or embellish any part of the body in deficit of lipids,
Anti-ageing,
Of oily skins,
Of acne-prone skin (prevention and treatment),
Anti-dandruff,
Acting on hair and nail growth,
Peeling,
Sunscreen,
Deodorizing,
Anti-seborrhea,
Anti-glycation,
For promoting re-epithelialization and/or regeneration of the skin or the lips and of the contour of the hair root or the nails, and/or
For improving the skin comfort affected by cold, UV or mechanical frictions.

Or furthermore to the following therapeutic treatments, including dermatological: anti-bacterial, anti-microbial, anti-inflammatory, anti-acne, against pimples, rosacea, lentigo, including hyperpigmentary dermatosis, eczema or impetigo.

Lightening, whitening, hydrating/moisturizing, anti-dandruff and anti-acne are more specifically aimed according to the invention.

DETAILED DESCRIPTION

A) Preparation Example of a Mixture of Unsaturated Dicarboxylic Acids of the Invention by Metathesis Metathesis Reaction For the metathesis reaction, 50 grams of methyl oleate purified to more than 90%, preferably stabilized with 100 ppm of tert-butylhydroquinone, were heated to a temperature of 100° C. under nitrogen. 200 ppm (final) of titanium isopropoxide (catalyst activator) are added under stirring. Umicore M73SIMES, ruthenium-based complex catalyst (5 ppm final in 100 µl of tetrahydrofuran) is then added. After about 5 minutes of reaction, the theoretical equilibrium (previously determined by gas chromatography) is reached.

2 g of activated bentonite are added to the reaction mixture to entrap the catalyst and the catalyst activator. The mixture is then filtered through a cellulose filter to remove the catalyst and enhancer, and the filtrate is recovered.

Purification

Fractional distillation is then conducted to separate the two reaction products (9-octadecene and dimethyl octadecenedioate) and the untransformed substrate (methyl oleate). This distillation is done under a vacuum of 1 to 10 mbar. Dimethyl octadecenedioate is collected/purified at a temperature between 210° C. and 220° C. This fraction has a purity greater than 85% (determined by gas chromatography).

Hydrolysis

The dimethyl octadecenedioate fraction from the distillation is hydrolyzed by saponification (KOH in ethanol/water under reflux at 70° C.), then cooled to 55° C. During a gradual acidification with phosphoric acid under stirring, the product of hydrolysis, octadec-9-ene-1,18-carboxylic acid, precipitates. It is then filtered and washed with water until the washings have a neutral pH. It is then dried under vacuum (10 mbar at about 60° C.) and finally purified by molecular distillation at 180° C. and 0.001 mbar. An antioxidant may be added at this final stage.

The mixture according to the invention thus obtained is a white solid, which can be used as an active ingredient in any cosmetic or dermatological composition. It is this mixture that is used in the in vitro and in vivo evaluations as well as in the below galenic formulas.

| Analysis/characterization of the obtained mixture according to the invention | |
|---|---|
| Parameter | Value |
| Acid value (mg KOH/g) | 345 |
| Saponification value (mg KOH/g) | 347 |
| Iodine value (g I/100 g) | 80 |
| Value of peroxydes (mmol O2/kg) | 10 |
| Melting point | 90-95° C. |
| % of octadec-9-ene-1,18-dicarboxylic acid | 94.4% |
| % of monocarboxylic acids | 0.3% |
| % of di or tri unsaturated dicarboxylic acids | 2.9% |
| % of saturated dicarboxylic acids | 2% |
| % of E isomer in the total weight of octadec-9-ene-1,18-dicarboxylic acid | 82% |
| % of Z isomer in the total weitht of octadec-9-ene-1,18-dicarboxylic acid | 18% |

A highly purified mixture of unsaturated dicarboxylic acids is therefore provided.

Used Methods:

(i) Iodine Value

The iodine value of the composition of unsaturated dicarboxylic acids is determined by the Wijs (AOCS) Official Method Tg 1-64 (1993) method and expressed as the number of grams of absorbed iodine per 100 grams of sample, in the defined test conditions.

(ii) Acid Value

The acid value of the composition of unsaturated dicarboxylic acids is measured using the AOCS Official Method Te 1a-64 (Reapproved 1997) and expressed as the number of milligrams of potassium hydroxide required to neutralize free fatty acids in 1 gram of sample.

(iii) Saponification Value

The saponification value of the composition of unsaturated dicarboxylic acid is measured using the AOCS Official Method: Tl 1a-64 (1997) and expressed as the number of milligrams of potassium hydroxide which reacts with 1 gram of sample in the defined conditions.

(iv) Fatty Acid Composition

The fatty acid composition of the unsaturated dicarboxylic acid composition according to the invention is determined by gas chromatography (GC). Prior to this analysis, the sample is methylated using the Combipal system. 8 mg of fatty acid sample are dissolved in 100 µl of methanol. 0.5 ml of BF3 catalyst (boron trifluoride) at 20% in methanol are added. The mixture is stirred and heated to 80° C. for 4 minutes. After cooling to room temperature, 600 µl of heptane and 600 µl of water are added. The two-phase system is stirred for 2 minutes, and the upper phase (heptane) was transferred to a clean tube, ready for analysis.

Instrumentation and Conditions of the Gas Chromatography (GC):

Column: CP-FFAP CB, length: 25 m, internal diameter: 0.32 mm, film thickness: 0.30 mm.

Temperature: 120° C. and 8° C. rise per minute to 250° C. (6.25 minutes)

Carrier gas: hydrogen.

Flow rate: 120 ml/min.

Injection: Split/µl.

Detection: F.I.D.

Pressure: 9 psi.

Duration of analysis: 22.5 minutes.

(v) Z Et E Isomer Composition

The methylated samples provided in (iv) above are also used for determining the E/Z ratio using the GC. The standard method for the determination of E and Z isomers of the monomethyl esters is not appropriate for the dimethyl esters. Thus, the isothermal oven temperature was increased from 160° C. to 210° C. and the analysis time is 15 minutes. The results are based on a comparison with a standard Z.

Instrumentation and Conditions of the GC:

Column: CP Sil 88, length: 25 m, internal diameter: 0.32 mm, film thickness: 0.20 µm.

Temperature: 210° C. (15 minutes)

Carrier gas: hydrogen.

Flow rate: 1.39 ml/min.

Injection: split ratio of 1:100.

Detection: F.I.D.

Pressure: 5.6 psi.

Duration of analysis: 15 minutes.

B) In Vitro Evaluations

The interest of the dermatological or cosmetic treatments of the active ingredient according to the invention by comparison with the ingredient of the prior art obtained by biotransformation as described above is illustrated by the in vitro tests given below. Comparative tested mixtures of dicarboxylic acid(s) are given in the following table:

| | Mixture according to the invention | Mixture according to prior art |
|---|---|---|
| % of octadec-9-ene-1,18-dicarboxylic acid | 94.4% | 60.8% |
| % of monocarboxylic acids | 0.3% | 5.6% |
| % of di or tri unsaturated dicarboxylic acids | 2.9% | 26.4% |
| % of saturated dicarboxylic acids | 2% | 6.8% |
| % of E isomer in the total weight of octadec-9-ene-1,18-dicarboxylic acid | 82% | 1% |
| % of Z isomer in the total weight of octadec-9-ene-1,18-dicarboxylic acid | 18% | 99% |
| Melting point | 90-95° C. | ≈57° C. |

Additional assays were realized with different intermediary combinations of these 2 mixtures to form compositions containing 25%, 40% and 60% of E isomer of octadec-9-ene-1,18-dicarboxylic acid (hereinafter referred to the octadecene dioic acid). They were tested in parallel with the invention mixture and the prior art mixture defined above.

1. Direct Effect on Pigmentation

The cosmetics industry is looking for compounds having depigmenting (whitening, depigmentation and skin lightening; elimination or reduction of freckles, age spots etc.). In vitro, it is possible to show such an effect by determining the melanin synthesized and/or the tyrosinase activity on melanocyte cultures with or without contact with the compounds to be evaluated. Another way to limit pigmentation is to slow down the transfer of melanosomes, via phagocytosis, from the melanocyte to neighbouring keratinocytes.

a) Inhibition of Melanin Synthesis and/or Decrease of Tyrosinase Activity on Human Melanocytes Protocol for Melanin Normal human melanocytes are cultured in their maintenance medium and then contacted with the products to be tested in the test medium for 10 days. After the contact, melanins are extracted from the cells and assayed by spectrophotometry (490 nm). An estimate of cell number is performed after cultivation using a protein assay by the BCA method. Melanin concentrations are normalized by the sample protein content.

Protocol for Tyrosinase

Normal human melanocytes are cultured in their maintenance medium and then contacted with the products to be tested in the test medium for 10 days. After the contact, the residual tyrosinase activity is measured in cell homogenates. An estimate of cell number is performed after cultivation using a protein assay. Tyrosinase activity is normalized by the sample protein content.

Results

TABLE 1

Melanogenesis inhibition compared to the control in normal human melanocytes.

| Concentration | Prior art mixture/ ingredient | Invention mixture/ ingredient |
| --- | --- | --- |
| 30 ppm | −16% | −26% |
|  | $p < 0.01$ | $p < 0.01$ |
| 50 ppm | −20% | −29% |
|  | $p < 0.01$ | $p < 0.01$ |
| 100 ppm | −22% | −36% |
|  | $p < 0.01$ | $p < 0.01$ |

The arbutine positive reference at 0.01% shows 33% inhibition compared to the control.

The two ingredients inhibit significantly and dose-dependently melanin synthesis in normal human melanocytes. Surprisingly the ingredient according to the invention provides better results that the ingredient of the prior art, at all tested doses.

TABLE 2

Variation of the tyrosinase activity relative to the % of E isomer in the total weight of octadecene dioic acid (E + Z) in normal human melanocytes in the presence of 50 ppm of octadecene dioic acid (n = 3)

| % of E isomer in the total weight of octadecene dioic acid | Variation in tyrosinase activity (%) | Significance |
| --- | --- | --- |
| 1 | 0 | dns |
| 25 | −22 | $p < 0.01$ |
| 40 | −18 | $p < 0.01$ |
| 60 | −20 | $p < 0.01$ |
| 82 | −20 | $p < 0.01$ |

No Cytotoxic Effect was Observed

No inhibition of tyrosinase activity is seen with the prior art mixture whereas with the invention mixture comprising the E isomer an inhibition is observed, with no dose effect.

b) Slowing Down the Transfer of Melanosome

Principle

Type B ultraviolet accelerate skin pigmentation and the transfer of melanosomes from melanocytes to neighboring keratinocytes by phagocytosis. Similarly, the keratinocyte growth factor (KGF) accelerates this phagocytosis. The moderation of this phagocytosis is known to promote skin lightening.

Protocol

Normal human keratinocytes (NHK) at confluence were rinsed and placed in a test medium for 24 hours. The cell layers were exposed to UVB in a buffer salt solution then were cultured during 48 h in the test medium containing or not the invention ingredient. During this period phagocytosis capacity was tested by adding fluorescent microbeads. After rinsing to remove non-phagocytosed beads, photos were taken by fluorescence microscopy and phagocytosis was quantified by image analysis. The number of cells was estimated using a fluorescent DNA stain. For the stimulation of phagocytosis by KGF, a procedure identical to the above was used, the cells being in contact with the KGF instead of being irradiated.

Results

TABLE 3

Decrease of phagocytosis UVB induced or KGF induced in NHK (n = 4)

|  |  | Variation (%) | Variation (%) |
| --- | --- | --- | --- |
| (—) UVB | Control | Reference (—) |  |
|  | Invention mixture: 20 ppm | −53%; $p < 0.01$ |  |
| UVB | Control | +72%; $p < 0.01$ | Ref. UVB |
|  | Invention mixture: 20 ppm |  | −59%; $p < 0.01$ |
| (—) KGF | Control | Reference (—) |  |
|  | Invention mixture: 20 ppm | −78%; $p < 0.01$ |  |
| KGF | Control | +52%; $p < 0.05$ | Ref. KGF |
|  | Invention mixture: 20 ppm |  | −86%; $p < 0.01$ |

No Cytotoxic Effect was Observed

The results show, as expected, that UVB and KGF significantly increase phagocytosis microbeads (phenomenon comparable to a transfer of melanosomes) of +72% and +52% respectively. The invention mixture decreases phagocytosis by keratinocytes either the basal level or after induction. With UVB the decline is −53% and −59%, respectively ($p<0.01$); with KGF the decrease is −78% and −86%, respectively ($p<0.01$).

These results show that a moderation of melanin production, a reduction of the residual activity of tyrosinase and phagocytosis, three clear indicators that would promote the invention mixture as a powerful skin lightening.

2. Effect on the Prevention of Cutaneous Aging a) Action on Reactive Oxygen Species (ROS) at the Cellular Level The excess of ROS in the cell provides an increase of immediate oxidative damages on biological material, on lipids, proteins, nucleic acids and sugars, and at long-term leads to cellular aging. Hence the constant search by the cosmetic industry of antioxidants that can act at the cellular level.

Evaluation of ROS was performed on human dermal fibroblasts (HDF) with DCFH-DA probe which, once in the cell, becomes fluorescent in contact with ROS (fluorescence level directly proportional to the amount of ROS).

Protocol

The fibroblasts are plated. After 24 h of attachment, cells are contacted with the products to be tested for 24 hours. The products are removed, the cell layers rinsed and the cells are "loaded" with the DCFH-DA probe. After rinsing, the cells are again contacted with the product to be tested and an oxidant ($H_2O_2$). A fluorescence reading is used to estimate the amount of ROS present in the cells. The fluorescence results are adjusted to the cell number.

Results

TABLE 4

Variation of the amount of intracellular ROS post-oxidative stress compared to the control

| Concentration | Ingredient of the prior art | Ingredient of the invention |
|---|---|---|
| 10 ppm | −31% | −54% |
|  | $p < 0.01$ | $p < 0.01$ |

The Trolox positive reference at 500 mM shows −72% inhibition compared to the control.

The two ingredients have a protective effect against oxidative stress on normal human fibroblasts. However, it is observed that the ingredient according to the invention gives better results that the ingredient of the prior art.

TABLE 5

Variation of intracellular ROS post-oxydative stress relative to the % of E isomer in the presence of 30 ppm of octadecene dioic acid (n = 3).

| % of E isomer in the total weight of octadecene dioic acid | Lipids Variation (%) | Significance |
|---|---|---|
| 1 | −33 | $p < 0.01$ |
| 25 | −61 | $p < 0.01$ |
| 40 | −49 | $p < 0.01$ |
| 60 | −55 | $p < 0.01$ |
| 82 | −54 | $p < 0.01$ |

No Cytotoxic Effect was Observed

The results show that using 25% of E isomer in the total weight of octadecene dioic acid, give a better decrease of intracellular ROS post-oxydative stress than the ingredient of the prior art (containing only 1% of E isomer octadecene dioic acid). This effect is not dose-dependent.

This antioxidant action is also a major player, even indirectly, in skin pigmentation.

b) Action on the Dermal Extra Cellular Matrix

Collagen I and elastin are the most abundant proteins in the dermis. It is essential to have a firm and elastic skin. The loss of density, thickness and elasticity of the dermis is related to a reduction of the synthesis of these macromolecules by dermal fibroblasts, the cells in charge of their production, during aging.

This determines the mechanical properties (elasticity, flexibility and firmness) of the skin.

It is thus important to stimulate the synthesis of these two macromolecules.

Immuno-Labelling of Cell Layers

Protocol

Normal human fibroblasts (NHF) in culture are contacted with the compound to test (or its excipient for the control) for 6 days. The synthesis of collagen I and elastin is quantified on photos after immuno-labelling of fixed layers. A counting of cell nuclei is realized using the DNA stain (Hoechst 33258), so as to adjust the result to the number of cells.

Results

TABLE 6

Variation of collagen I synthesis (NHF layers) compared to the control.

| Concentration | Prior art ingredient | Invention ingredient |
|---|---|---|
| 20 ppm | +45.5% | +101.9% |
|  | $p < 0.01$ | $p < 0.01$ |

Both ingredients stimulate collagen synthesis in normal human fibroblasts. It is observed that the ingredient according to the invention gives better results that the ingredient of the prior art.

TABLE 7

Variation of collagen I synthesis (NHF layers) relative to the % of E isomer in the presence of 20 ppm of octadecene dioic acid, compared to the control (n = 3).

| % of E isomer in the total weight of octadecene dioic acid | Variation in Tyrosinase activity (%) | Significance |
|---|---|---|
| 1 | +122 | $p < 0.01$ |
| 40 | +142 | $p < 0.01$ |
| 82 | +164 | $p < 0.01$ |

No Cytotoxic Effect was Observed

The results confirm that the observed effect is dependent on the % of E isomer of octadecene dioic acid present in the mixture tested.

TABLE 8

Variation of elastin synthesis (NHF layers) compared to the control.

| Concentration | Invention ingredient |
|---|---|
| 3 ppm | +179% |
|  | $p < 0.01$ |

This result shows that the invention ingredient stimulates elastin synthesis in normal human fibroblasts.

3. Effect on Skin Dryness. Improving Barrier Function of the Epidermis and Stratum Corneum a) Synthesis of Hyaluronic Acid by Human Keratinocytes The main interest of hyaluronic acid is its role as a moisturizer for the skin.

Hyaluronic acid is present in the intercellular spaces of the basal and spinous layers, but absent from the upper layers (granular and cornea). Its skin moisturizing role will therefore be positioned at the level of the lower epidermis layers.

Protocol

Human keratinocytes are cultured for 24 h. The cells are contacted with the products to be tested or their excipient for 3 days. The culture supernatants are recovered and a dosage of the amount of hyaluronic acid is achieved. Retinoic acid is used as a positive control. Quantification of cells present on the layer is carried out with the DNA dye (Hoechst 33258), so as to adjust the dosages to the number of cells.

TABLE 9

Variation of the synthesis of hyaluronic acid (surpernatants of human keratinocytes) compared to the control.

| Concentration | Prior art ingredient | Ingredient of the invention |
|---|---|---|
| 10 ppm | +40%<br>$p < 0.01$ | +37%<br>$p < 0.01$ |

Retinoic Acid, the Positive Control, at 1 μm Gives a Stimulation of +106%; $p<0.01$ vs. Control.

The 2 ingredients stimulate the synthesis of hyaluronic acid on human keratinocytes. They therefore participate in improving the hydration and barrier of the epidermis.

b) Keratinocyte Differentiation

An active able to stimulate the keratinocyte differentiation is particularly useful for strengthening the skin barrier effect.

Protocol

Confluent human keratinocytes in culture are contacted with the product to test in a specific medium to promote the establishment of intercellular junctions and thus improve the anchoring of the differentiated cells to the underlying cells and to the culture dish. A negative control is performed in the same medium.

The appearance of differentiation is assessed visually at 3, 5 and 7 days.

Results

It is observed visually that the ingredient according to the invention as well as the prior art ingredient cause an acceleration of the differentiation at 10 and 20 ppm compared to the control. At all observation times, stimulation of the formation of typical structures of the upper layers of the epidermis is noticed with the 2 ingredients (presence of branched structures and in multilayers that are characteristics of the protein-lipid rigid matrix of the cornea envelope). The cells are associated in important cohesive aggregates, sometimes interconnected together by a network. This is not observed at the same times on the control layers.

c) Increase of Key Molecules to Reinforce Skin Barrier Function

During keratinocyte differentiation a number of syntheses converge to create the cornified cell envelope, in terms of both the production of corneocytes gorged with a cross-linked protein matrix and the production of specific lipids. This cornified cell envelope (stratum corneum) is a hydrated proteo-lipid barrier and a natural sunscreen against UV radiations. Involucrin, loricrin and ceramides are essential molecules for the formation of this stratum corneum.

Protocol

Just confluent normal human keratinocytes were contacted with the ingredient of the invention in a test medium. After 7 days culture, the layers are rinsed, fixed and loricrine, involucrine and ceramides are identified by immuno-fluorescence and quantified by image analysis. An Hoechst counter staining of nuclei completes the study and weighs these results.

TABLE 10

Effect of the ingredient of the invention on involucrin synthesis in human keratinocytes (n = 3 and 15 photos per case)

| Involucrin IMF | Cell Number variation | Variation % |
|---|---|---|
| Control | Reference | Reference |
| Invention ingredient | 15 ppm | +775 ($p < 0.01$) |

TABLE 11

Effect of the invention product on loricrin synthesis in human keratinocytes (n = 3 and 15 photos per case)

| Loricrin IMF | Cell Number variation | Variation % |
|---|---|---|
| Control | Reference | Reference |
| Invention ingredient | 15 ppm | +120% ($p < 0.01$) |

TABLE 12

Effect of the invention ingredient on ceramide 2 synthesis in human keratinocytes (n = 3 and 15 photos per case)

| Ceramide 2 IMF | Cell Number variation | Variation % |
|---|---|---|
| Control | Reference | Reference |
| Invention ingredient | 15 ppm | +423% ($p < 0.05$) |

The product according to the invention strongly stimulates the involucrin, the loricrin and ceramide 2 synthesis, and therefore differentiation of keratinocytes and efficiency of the skin barrier.

4. Test in Relationship with a Plumping/Volumizing Action

Some cosmetic compounds are designed to promote the installation of subcutaneous fat for better aesthetics and greater volume.

In this perspective, in vitro tests aiming to show an increase in adipocyte differentiation (with glycerol-3-phosphate dehydrogenase or G3PDH as the key enzyme of this differentiation) on pre-adipocyte cultures were implemented. Other in vitro assays seek to show slower lipolysis on adipocyte cultures to validate the effectiveness of these compounds.

a) G3PDH Activity on Human Adipocytes

Protocol

Human pre-adipocytes are seeded and induced to differentiate with a specific mixture of inducers (without indomethacine*) in the presence or absence (negative control) of the products to be tested. After 10 days, the cultures are stopped and the residual G3DPH activity is measured by spectrophotometry on a cellular lysate. In parallel, an estimation of the cell amount is realized by Hoechst assay to weigh the obtained data.

Indomethacin, a PPAR agonist is removed from the differentiation inducers to release these receptors and demonstrate the effect of products acting on this path (as with pioglitazone=positive control).

Results

TABLE 13

Variation of the G3PDH activity compared to the control (human adipocyte layers)

| Concentration | Prior art ingredient | Ingredient of the invention |
|---|---|---|
| 30 ppm | +262%<br>$p < 0.01$ | +299%<br>$p < 0.01$ |

The Pioglytazone positive control at 10 μm shows a stimulation of +712%; $p<0.01$ vs. control.

Both ingredients stimulate the G3PDH activity on human adipocytes.

b) Measurement of the Lipolysis on Human Adipocytes

Protocol

Human pre-adipocytes are cultured and induced to differentiate with a mixture of specific inducers. When mature adipocytes are obtained well loaded in triglycerides, the cells are contacted with the products to be tested (or their excipient). After 3 h of incubation, supernatants are recovered and the amount of released glycerol, from the hydrolysis of intracellular triglycerides, is measured.

TABLE 14

| | Variation of released glycerol compared to the control (human adipocytes) | |
|---|---|---|
| Concentration | Prior art ingredient | Ingredient of the invention |
| 100 ppm | −36% $p < 0.05$ | −37% $p < 0.05$ |

Both ingredients are able to slow down lipolysis on human adipocytes.

5. Test in Relationship with Oily Skins/Reduction of Sebum Production

Oily skin is associated with a too abundant sebum production by cells called sebocytes. Too much sebum often leads to modify the properties of the skin and scalp, for example in enhancing the formation of pimples and blackheads.

Dead skins, mired with sebum, trap bacteria and yeast (as *Malassezia furfur* in the scalp causing dandruff) that feed and proliferate.

Decreased Lipid Synthesis in the Sebocyte

Protocol

Human sebocytes (woman 26 years old, face) were seeded in a specific growth medium. After reaching confluence, the cells are contacted with the test product according to the invention for 48 hours. After removing the media, cell layers were incubated with Nil Red marker of intracellular lipids to estimates by a fluorescent measurement the amount of lipid present in cells. The estimate of the viability is performed on the corresponding cell layer using another fluorescent dye.

TABLE 15

Variation of the synthesis of lipids in sebocytes relative to the % of E isomer in the presence of 60 ppm of octadec-9-ene-1,18-dicarboxylic acid, relative to the control (n = 3).

| % of E isomer in the total weight of octadecene dioic acid | Lipids Variation (%) | Significance |
|---|---|---|
| 1 | −17 | nds |
| 25 | −11 | nds |
| 40 | −32 | $p < 0.01$ |
| 60 | −33 | $p < 0.01$ |
| 82 | −37 | $p < 0.01$ |

No Cytotoxic Effect was Observed

The mixture according to the invention can be used to treat skin disorders associated with oily skin which appear bright shiny, with the presence of pimples and blackheads. The scalp can be "cleaned up" with less sebum, ground for bacteria and yeast, and trap for dandruff.

6. Indirect Control of Pigmentation Inducers. Decrease of Pro-Pigmentary and Pro-Inflammatory Lipids Production Protocol Subconfluent human keratinocytes are contacted with the products to be tested for 24 hours. Then the cells are washed in a buffer and irradiated in the same buffer with UVB. At the end of this phase, the cells are again contacted with the test products for 24 h. Finally, the media are recovered and the amount of PGE2 synthesized are measured by an ELISA method. The cell layers are used to estimate the cell number by the MTT method.

TABLE 16

Variation of released of PGE2 UVB induced (human adipocytes) in the presence of the ingredient of the invention, relative to the control (n = 3).

| | | Variation (%) | Variation (%) |
|---|---|---|---|
| (−) UVB | Control (−) UVB | Référence (−) UVB | |
| UVB | Control UVB | +376%; $p < 0.01$ | Réf. UVB |
| | Invention ingredient 10 ppm | | 47%; $p < 0.01$ |
| | Invention ingredient 30 ppm | | −69%; $p < 0.01$ |

No Cytotoxic Effect was Observed

Results

The results show that stress UVB significantly increases the production of PGE2 (+376%). The invention ingredient decreases in KHN this production of −47% and −69% for 10 and 30 ppm respectively (p<0.01). This anti-inflamatory action is also a major player, even indirectly, in skin pigmentation.

7. Anti-Bacterial Action—Prevention and Treatment of Acne Prone Skins

Protocol:

Strain: *Propionibacterium acnes*

Culture medium (solid and liquid): modified Medium 20

Range of tested concentrations up to 5000 ppm (dilution of ND in DMSO)

In solid condition, the 2 following methods were tested:

Method 1: The mixture of the invention is mixed to the culture medium before solidification (to have the final concentration of interest). 5 μL strain are inoculated by dropping culture with titrated cell number. The Petri Dishes are then incubated in anaerobic conditions at 37° C. The diameter of the growth spot is measured: the more the molecule is active the more the spot is small (no spot for total inhibition).

Method 2: 200 μL strain are spread on solid medium. A cellulose disc is put onto solid medium and 10 μL of the mixture of the invention are dropped onto the cellulose disc. The Petri Dishes are then incubated in anaerobic conditions at 37° C. in anaerobic jar. The indicator of a positive test is the growth inhibition by seeing an inhibition area (the spot diameter of inhibition is measured).

In liquid condition, the strain is incubated in liquid modified medium 20 with different cell concentration and/or of the invention ingredient concentration, under anaerobic conditions into Plasma Bottle. The growth profile is monitored during 96 hours by getting absorbance value at 600 nm.

Results:

A positive activity is shown: a reduced amount of cells (less absorbance, less cell number, less dry weight, less cell viability) and/or an extended lag phase and/or a reduced growth rate (or doubling time) is observed.

C) Examples of Galenic Formulations

As mentioned above in the description, it is obvious that different cosmetic formulations can be implemented that can integrate the active ingredient of the invention. A cream formula is given below by way of example.

Additional active ingredients, in support and/or complement of the activity of the active ingredient of the invention, can be added in the proper phase of the formulations according to their hydrophobic or hydrophilic nature. These ingredients can be of any class according to their(s) function(s), site of application (body, face, neck, chest, hands, hair, eyelashes, eyebrows, body hair, etc.), the desired final effect and the targeted consumer, for example anti-aging, anti-wrinkle, moisturizing, lightening, anti-acne, to treat under dark circles, firming, anti-glycation, slimming, calming, myo-relaxant, anti-redness, anti-stretch marks, etc.

Example of Day Cream (Used for the In Vivo Test on African Skins Given Below)

| Product | % | INCI name |
|---|---|---|
| Phase A | | |
| H₂O | Qsp100 | Water |
| Potassium sorbate | qs. | Potassium Sorbate |
| Phase B | | |
| Butylene Glycol | 3.00 | Butylene Glycol |
| Octanediol | 0.50 | Caprylyl Glycol |
| Phase C | | |
| Phenoxyethanol | qs. | Phenoxyethanol |
| Keltrol CG-SFT ™ | 0.60 | Xanthan Gum |
| Supercol GF ™ | 0.20 | Cyamopsis Tetragonoloba (Guar) Gum |
| Phase D | | |
| Brij S2-SS-(RB) ™ | 1.00 | Steareth-2 |
| Crodafos MCA-SO-(RB) ™ | 2.00 | Cetyl Phosphate |
| Stearic acid | 2.50 | Stearic Acid |
| Laurocapram | 2.00 | Laurocapram |
| BRB CM-56 ™ | 3.00 | Cyclopentasiloxane & Cyclohexasiloxane |
| Arlacel 170-PA-(RB) ™ | 3.00 | Glyceryl Stearate & PEG-100 Stearate |
| Crodamol GTCC-LQ-(MV) ™ | 3.00 | Caprylic/Capric Triglyceride |
| Ingredient of the invention | 4.00 | |
| Phase E | | |
| H₂O | 4.50 | Water |
| NaOH 30% | 0.90 | Sodium Hydroxide |
| Phase F | | |
| Fragrance | 0.10 | Fragrance |

Protocol:

Weigh phase A. Weigh phase B and melt at 45° C., then let cool to 25° C. Add one by one the compounds of phase C in phase B. Mix well. Add phase B+C in phase A under propeller stirring v=500 rpm for 30 minutes minimum. Heat phase A+B+C to 85° C. in a water bath. Heat phase D at 85° C. in a water bath. Add phase D into phase A+B+C under Staro stirring v=3000 rpm. Add phase E under Staro stirring, mix well. Add phase F below 35° C. Mix well.

Example of Day Cream (Used for the In Vivo Test on Asiatic Skins Given Below)

| Product | % | INCI Name |
|---|---|---|
| Phase A | | |
| H₂O | Qsp100 | Water |
| Carbopol Ultrez 10 ™ | 0.30 | Carbomer |
| Phase B | | |
| Brij S2-SS-(RB) ™ | 0.40 | Steareth-2 |
| Brij S10-SO-(RB) ™ | 1.20 | Steareth-10 |
| Crodafos CES-PA-(RB) ™ | 4.00 | Cetearyl Alcohol & Dicetyl Phosphate & Ceteth-10 Phosphate |
| Laurocapram | 2.50 | Laurocapram |
| Cyclopentasiloxane & Cyclohexasiloxane | 2.00 | Cyclopentasiloxane & Cyclohexasiloxane |
| Crodamol OSU-LQ-(RB) ™ | 4.00 | Diethylhexyl Succinate |
| Crodamol AB-LQ-(RB) ™ | 3.00 | C12-15 Alkyl Benzoate |
| Ingredient of the invention | 2.50 | — |
| Phase C | | |
| Glycerin | 4.00 | Glycerin |
| Octanediol | 0.50 | Caprylyl Glycol |
| Phase D | | |
| Phenoxyethanol | qs | Phenoxyethanol |
| Phase E | | |
| Potassium sorbate | qs | Potassium Sorbate |
| Phase F | | |
| H₂O | 4.00 | Water |
| NaOH 30% | 0.40 | Sodium Hydroxide |
| Phase G | | |
| Fragrance | 0.10 | Fragrance |

Protocol:

Phase A: Sprinkle carbomer in water and let swell without stirring for 30 minutes. Heat phase A at 85° C. in a water bath. Weigh phase B and heat at 85° C. in a water bath. Weigh and melt phase C at 45° C. Add the phase D into phase C, previously cooled, mix well. Add phase C+D in phase A under normal agitation rotor stator mixer v=500 rpm. Mix well. Pour the phase B in the previous phase with rapid stirring rotor stator mixer v=1000 rpm. Mix well. Extemporaneously add phase E, homogenize. Add phase F, homogenize. Add phase G, homogenize.

Examples of ingredients which may be added to this type of cream formula in one of the phases or extemporaneously according to their hydrophobic or hydrophilic physical property, at a certain % depending on their concentration and the desired effect:

LUMISHERE™: active ingredient marketed by Sederma (WO2004/024695). It is the combination of diacetyl-boldine (DAB) encapsulated in polymethylmethacrylate microcapsules and titanium dioxide modified with manganese (TiO₂Mn). The TiO₂Mn gives the skin a unifying, mattifying and luminous effect and DAB provides a physiological lightening effect. 4% of this ingredient may for example be added at the end of the formulation.

RUBISTEM™: anti-redness active ingredient comprising an extract of *Centella asiatica*, marketed by Sederma, which protects blood capillary and extracellular matrix from oxidizing attacks and collagenase; 2% of this ingredient may be added at the end of the formulation before phase E.

NG Birch Sap™: raw sap from birch sapwood; skin toning and moisturizing marketed by Sederma.

MATRIXYL™3000: peptide-based anti-wrinkle ingredient marketed by Sederma (WO2005/048968) comprising two matrikines Pal-GHK and Pal-GQPR, which in synergy helps repairing skin damages caused by aging.

MATRIXYL synth'6™: peptide-based anti-wrinkle ingredient marketed by Sederma (WO2010/082175) which helps repair skin damage caused by aging.

Tocopherol (vitamin E) or a-lipoic acid (ALA): active with anti-oxidant and anti-radical properties. 0.5% by weight can be added for example to the formulation.

PRODIZIA™: active ingredient marketed by Sederma (WO2013/046137), comprising an extract of *Albizia julibrissin*, fighting the signs cutaneous fatigue: dark circles, under eye bags, dull complexion and drawn features, by repairing and protection the skin against the caused by damages of glycation and glycoxydation.

Niacinamide (B3 vitamin), Retinol, Resveratrol, DHEA: anti-aging actives, including anti-wrinkle. 0.5% by weight of Retinol, Resveratrol or DHEA may be for example extemporaneously to the formulation. 10 wt % of Niacinamide 10% in water can for example be added to the formulation.

Hexamidine: antibacterial active that may be added to the formulation at 0.5% by weight.

Among other particularly interesting galenic forms for the implementation of the cosmetic treatment according to the invention, there may be mentioned:

A mask form, with as examples of additional ingredients:

SEBULESS™: purifying sebo-regulator ingredient comprising a *Syringa vulgaris* extract, marketed by Sederma, which mattifies and refreshes complexion, fades the inflammatory blemishes.

YEAST WALLS™: active ingredient based on cell membranes with high enzymatic activity, marketed by Sederma, having anti-seborrhea activity, an effect on the texture and the complexion of the skin and flexibility.

AQUALANCE™: osmo-protector moisturising active ingredient marketed by Sederma (WO2009/104118) comprising homarine and erythritol. 4% by weight may be added for example at the end of formulation.

Ac-Net™: an active sold by SEDERMA (WO2003/028692) offering a complete treatment of oily and acne-prone skins.

A serum form (fluid emulsion), with as examples of additional ingredients:

RESISTEM™: anti-aging marketed by Sederma (WO 2012/104774), helping the skin to build its own anti-aging defense system, based on an extract obtained by cell culture of *Globularia cordifolia* plant.

MARUCELL™: active ingredient against pollution and antioxidant marketed by Sederma comprising an extract of *Marrubium vulgare*.

NG UNSAPONIFIABLE SHEA BUTTER™: active ingredient marketed by Sederma with nourishing and protective properties for the treatment of skin damaged by the environment.

VENUCEANE™: active marketed by Sederma (WO2002/066668) comprising a *Thermus thermophiles* biotechnological extract, that prevents visible signs of photo-aging (spots, wrinkles, dryness . . . ), protects cell structures from damages caused by UV and strengthens skin integrity.

EVERMAT™: active marketed by Sederma (WO2007/029187), which decreases the secretion of sebum and thus participates in the treatment of oily skin. 4% of this ingredient may for example be added to the formulation.

WONDERLIGHT™: active marketed by Sederma (Caprylic/Capric Triglyceride (and) *Humulus lupulus* (Hops) Strobile), which helps reduce hyperpigmentation accentuated by age and stress. 3% of this ingredient dissolved in Optasense G82 (Croda) can be added to the formulation.

The addition of OSMOCIDE 4™, active marketed by Sederma (WO 97/05856—Glycerin, Water (Aqua) (and) Caprylyl Glycol, Carbomer, Acrylates/C10-30 Alkyl Acrylate Crosspolymer) reduces the concentration of traditional conservatives.

A cleaning lotion form, with as examples of additional ingredients:

ECODERMINE™: active ingredient marketed by Sederma including an association of lactitol and xylitol, aimed to fight skin problems due to microbial imbalance (acne-prone skin, dryness, itching) by preserving the natural mechanism of skin defense.

HAIRSPA™: Scalp moisturisation and soothing active ingredient marketed by Sederma comprising lactitol and xylitol in glycerin, acts on skin microflore balance to fight against scalp discomfort (dryness, itching, dandruff, and irritations).

A milk form, with as examples of additional ingredients:

LEONTOCELL™: anti-wrinkle active marketed by Sederma comprising an extract of *Leontopodium alpinum* (Edelweiss).

LEGANCE™: anti-aging active marketed by Sederma (WO2013/105047), corresponding to a *Zingiber zerumbet* Smith extract obtained by $CO_2$ supercritical in a water-soluble excipient and titrated in zerumbone ingredient. It is a global anti-aging ingredient for legs. It improves their appearance and comfort by reducing water retention, improving microcirculation and refining adipose tissue.

INTENSLIM™: slimming active ingredient marketed by Sederma (WO2013/105048) corresponding to a synergistic combination of extracts obtained by *Globularia cordifolia* plant cell culture, *Zingiber zerumbet* Smith titrated in zerumbone obtained by supercritical $CO_2$ extraction and vegetable caffeine.

A gel form (for example for the eye contour which is a particularly sensible zone), with as examples of additional ingredients:

EYELISS™: active ingredient marketed by Sederma (WO2003/068141) that helps prevent against the appearance of bags under the eyes. It combines three components: hesperidin methyl chalcone reducing capillary permeability, Valyl-Tryptophan (VW) dipeptide which promotes lymphatic circulation and Pal-GQPR lipopeptide that improves firmness, elasticity and reduces inflammation.

BEAUTIFEYE™: active ingredient marketed by Sederma; an association of an *Albizia julibrissin* extract and darutoside extracted from *Siegesbeckia orientalis*, lifts the upper eyelid, reduces crow's feet wrinkles, fades away dark circles and diminishes puffiness.

Anti-Dandruff Shampoo

| Product | % | % | INCI name |
|---|---|---|---|
| Phase A | | | |
| H₂O | Qsp100 | Qsp100 | Water |
| Citric acid | 0.24 | 0.24 | Citric Acid |
| Citrate Trisodic | 1.20 | 1.20 | Sodium Citrate |
| NaCl | 0.50 | 0.50 | Sodium Chloride |
| Phase B | | | |
| Butylene Glycol | 5.00 | 5.00 | Butylene Glycol |
| Preservative | qs | qs | — |
| Activsoft S ™ | 0.30 | 0.30 | *Cyamopsis Tetragonoloba* (Guar) Gum |
| Keltrol CG-SFT ™ | 0.50 | 0.50 | Xanthan Gum |

-continued

| Product | % | % | INCI name |
|---|---|---|---|
| Phase C | | | |
| Empicol ESB 3/6M ™ | 30.00 | 30.00 | Sodium Laureth Sulfate |
| Plantacare 818 UP ™ | 5.00 | 5.00 | Coco Glucoside |
| Crodateric CAB-30-LQ-(MH) ™ | 8.00 | 8.00 | Cocamidopropyl Betaine |
| Crodasinic LS-30 ™ | 10.00 | 10.00 | Sodium Lauroyl Sarcosinate |
| Phase D | | | |
| Ingredient of the invention | 1.00 | 4.00 | |
| Cithrol EGMS-PA-(SG) ™ | 3.00 | 6.00 | Glycol Stearate |
| Phase E | | | |
| H₂O | 10.00 | 10.00 | Water |
| Zinc Pyrion 48% | 2.00 | 2.00 | Zinc Pyrithione |
| Phase F | | | |
| Fragrance | 0.10 | 0.10 | Fragrance |

Protocol:

Weigh phase A and stir under propeller v=200 rpm. Weigh and homogenize phase B. Add phase B into phase A under propeller stirring; let the gel swallow during 1 hour. Weigh phase C and homogenize. Add phase C into phase A+B under propeller stirring v=300 rpm. Heat phase A+B+C at 85° C. in a water bath. Heat phase D at 85° C. in a water bath. Add phase D into phase A+B+C under slow Staro stirring v=1000 rpm, homogenize well. Below 35° C., add phase E, under slow Staro stirring v=600 rpm. Add phase F, homogenize well.

Anti-Acne and Repairing Stick

| Product | INCI name | % | % |
|---|---|---|---|
| Phase A | | | |
| Crodacol C90-PA-(RB) ™ | Cetyl Alcohol | 24.00 | 24.00 |
| Syncrowax HRC-PA-(RB) ™ | Tribehenin | 5.00 | 3.00 |
| Span 60-PW-(MV) ™ | Sorbitan Stearate | 2.00 | 2.00 |
| NG Unsaponifiable shea butter | Butyrospermum Parkii (Shea) Butter Unsaponifiables (and) Butyrospermum Parkii (Shea) Butter | 1.50 | 1.50 |
| Ingredient of the invention | | 1.00 | 4.00 |
| Phase B | | | |
| Butylene Glycol | | Qsp 100 | Qsp 100 |
| Phenoxyethanol | | Qs | Qs |
| Crodesta F160-PW-(RB) ™ | Sucrose Stearate | 2.00 | 2.00 |
| Phase C | | | |
| Fragrance | | 0.20 | 0.20 |

Protocol: Weigh phase A and heat at 85° C. Weigh and mix phase B. Heat phase B at 85° C. until the powder is completely dissolved. Mix phase B to phase A and homogenise well. Weigh and homogenize phase C. Add phase C to phase A+B at about 50° C. Mix and pour into molds extemporaneously.

D) In Vivo Evaluations

The lightening/whitening activity of the active ingredient according to the invention has been shown in the two in vivo tests described below, one on African skins, and the other on Asiatic skins.

A day cream prepared according to the example described above (Part C), with 4% of the active ingredient according to the invention was used for these tests, in comparison with a placebo cream prepared by replacing the active ingredient according to the invention with water.

1) Test on African Skins

Principle

The test was conducted on a panel of 23 persons with African skin type and Fitzpatrick VI (30% tolerated V) phototype, male or female, healthy, particularly without skin problem, aged 22 to 43 years (average: 32 years). The test lasted 56 days (measurements and assessments made at T0, T28 and T56 days).

The evaluation was conducted by the so-called method of digital photographs of the face to colorimetric analysis (VISIA CR, Canfield), associated with a self-assessment questionnaire by volunteers.

Particular Non-Inclusion Criteria

A number of criteria for "good health" were verified in volunteers before the test: not being treated for diabetes, have no thyroid problems, skin hypersensitivity, allergic to certain cosmetic ingredients, not being under medical treatment due to a chronic illness or being under medical treatment during the study with aspirin-based products, anti-inflammatories, antihistamines, corticosteroids. Volunteers were also asked not to have undergone a general anesthesia of more than an hour in the 6 months preceding the test.

For female volunteers, it was asked:

Not having started, changed or stopped hormone therapy within 3 months before the test, Not to be pregnant, not to breastfeed, having stopped breastfeeding more than 3 months before the test)

It was asked to all volunteers

Not to have taken medical treatment can that could lead to hyperpigmentation of the skin during the 6 months preceding the test, Not to have used a cosmetic treatment in the week before the test, Not to have applied depigmenting product during the 4 weeks before the test, Not to apply any other cosmetic product than the products of the test on the study area (face) during the test.

Study Type and Duration

The study was made in single-blind: the volunteers are not aware of the type of tested product.

It is a contralateral comparative study in which the obtained results after applying the cream of the invention on a test area (right part of the face, for example) are compared with the results obtained after applying the placebo cream on another test area (left part of the face).

Each volunteer is thus its own reference and the results obtained at the 2 evaluation times are compared with those obtained at T0.

The creams were applied to the face in a twice daily massage for 56 days.

The synopsis of the study can be summarized according to the below table:

| T0 | T 28 days | T 56 days |
|---|---|---|
| Photos for a colorimetric analysis | Photos for a colorimetric analysis Self-evaluation | Photos for a colorimetric analysis Self-evaluation |

Statistical Analysis:

For the colorimetric analysis, whether it was the change over time for each cream or the comparison between the two products, the normality of the distributions was previously checked with a test of Shapiro-Wilk (significance level set at 1%).

Statistical studies were then performed using the Student t test (normal distributions) or with a non-parametric Wilcoxon test (if normality is rejected). In the 2 cases the tests were performed on bilateral paired series. The level of significance of the results was set at 5%.

For the treatment of the questionnaires, each product (placebo cream or cream containing the active ingredient according to the invention) provided 2 percentages: one evaluating the percentage of favorable opinion, the other the percentage of negative opinions (taking into account the frequency of each response). The statistical treatment of differences (between favorable and unfavorable opinions) was evaluated by the Chi-2 test with a significance level set at 5%.

Protocol

1. Digital Photographs of the Face for the Colorimetric Analysis (Visia-CR™)

The acquisitions were made with a VISIA-CR™ device.

The VISIA-CR is a device capable to acquire up to 7 standardized digital images of high resolution of the entire face in one take. These 7 images can visualize facial skin characteristics such as texture, color, brightness, "photo-damage", vascular features, fine lines and wrinkles and finally porphyrins (*P. Acnes*).

Photographs were taken of the left and right sides (45 degree angle) and front, of the face, in reproducible and standardized lighting, temperature and hygrometry conditions. The visualization of the original photograph (T0), at later times, guarantees a good repositioning of the subject.

Analysis of the Color of Black Skin:

The parameters: L* (relative brightness between total darkness 0 and absolute white 100), a* (on a red-green spectral axis) and b* (on a yellow-blue spectral axis) are determined from the RGB values (Red-Green-Blue) digital photos.

ITA° (Individual Typological Angle)=Arctg[(L*−50)/b*]×(180/π)

These parameters are determined on a region of interest set on each half-face of the face at T0, T28 days and T56 days.

For a lightening effect on black skins, the analysis is based on observed changes in the L* parameter reflecting the luminosity (brightness) of the skin (amount of white) and on the ITA° parameter reflecting the degree of pigmentation of skin.

A significant increase of these two parameters on the half-face receiving the day cream containing the active ingredient according to the invention, in comparison with the half-face treated with the placebo cream, reveal a lightening effect.

2. Self-Evaluation Questionnaires

The volunteers had to fill in a questionnaire at T28 and T56 days (two questionnaires at each examination time, one for each half-face) to evaluate their opinion on the effectiveness of the tested products.

Results

TABLE 17

Comparison of the differences between T0, T28 and T56 for the day cream comprising the active ingredient of the invention versus the placebo cream for the L* parameter (Brightness).

| | L* (Brightness) | | | | | |
|---|---|---|---|---|---|---|
| | Placebo | | | Cream of the invention | | |
| | T0 | T28 | T56 | T0 | T28 | T56 |
| Mean | 44.13 | 44.74 | 44.26 | 43.48 | 45.21 | 45.48 |
| Standard deviation | 5.82 | 5.98 | 5.91 | 5.68 | 6.12 | 5.65 |
| Variation vs. T0 | | 0.61 | 0.13 | | 1.73 | 1.99 |
| % variation vs. T0 | | 1.4 | 0.3 | | 4 | 4.6 |
| Significance | | p < 0.05 | dns | | p < 0.01 | p < 0.01 |
| Significance vs. placebo | | | | | p < 0.05 | p < 0.01 |

The statistical analysis of the values compared to T0 show significant differences, at the two evaluation time, between the two half-faces, for the L* parameter. For the cream of the invention, the increase was +4% and +4.6% respectively after 28 days and 56 days; against +1.4% and +0.3% for the placebo cream.

TABLE 18

Comparison of the differences between T0, T28 and T56 for the day cream comprising the active ingredient of the invention versus the placebo for ITA ° parameter (Pigmentation).

| | ITA ° (Pigmentation) | | | | | |
|---|---|---|---|---|---|---|
| | Placebo | | | Cream of the invention | | |
| | T0 | T28 | T56 | T0 | T28 | T56 |
| Mean | −21.34 | −19.06 | −20.60 | −23.35 | −17.24 | −16.28 |
| Standard deviation | 20.30 | 20.82 | 20.68 | 19.74 | 21.47 | 19.77 |
| Variation vs. T0 | | 2.28 | 0.74 | | 6.11 | 7.07 |
| % variation vs. T0 | | 10.7 | 3.5 | | 26.2 | 30.3 |
| Significance | | p < 0.05 | dns | | p < 0.01 | p < 0.01 |
| Significance vs. placebo | | | | | p < 0.05 | p < 0.01 |

The statistical analysis of the values compared to T0 show significant differences, at the two evaluation time, between the two half-faces, for the ITA° parameter. For the cream of the invention, the evolution was +26.2% and +30.3% respectively after 28 days and 56 days; against +10.7% and +3.5% for the placebo cream.

In conclusion, the active ingredient of the invention provides to the day cream a significant lightening effect measured here by a parameter measuring skin brightness (clarity) and another parameter connected to skin color.

From the Evaluation Questionnaires, it Appears:

In terms of cosmetic efficacy, after 56 days of testing, that the day cream containing the active ingredient of the invention is recognized as providing a lighter skin by 87% of the panel (significant result with p<0.05), while the placebo cream collects only 65% positive opinions (not significant).

At the end of the study, the overall judgment is in favor of the cream according to the invention (significant satisfaction rating of 74%) while the placebo cream collects only 65% of satisfaction (not significant).

2) Test on Asiatic Skins

Principle

The evaluation of the efficacy of the composition according to the invention was performed on a panel of 25 female volunteers of Asian type, average age of 47 years (21-60 years), during which the colour of the face was measured by spectrophotometry.

Special Inclusion Criteria

The Asian type volunteers had to have spots on the cheeks, at least one of a minimum diameter of 3 mm on each side. Their skin could be of any type (dry, oily, normal) but not sensitive. During the test, strict sun protection was required (hat, umbrella) and it was not allowed to start using a sunscreen product or changing the protection factor if the volunteer was used to apply one.

Study Type and Duration

The studies were conducted on single-blind on the face. A cream according to example. (or its placebo) was applied in contralateral. The two creams were applied twice daily for 3 weeks. The front received no product and has been used as a control in the study.

The statistical studies were performed using the Student t test or if necessary with a non-parametric Wilcoxon test. Bilateral tests were performed on paired series.

Protocol: Spectrophotometry Evaluation

A CM700d spectrophotometer (Konica Minolta, Japan) was used in this study. This device often used in cosmetology, measures the reflection of light between 400 and 700 nm (visible light). It can work in the referenced colorimetric space CIELab, which defines a color by 3 coordinates:

L*: from 0 (black) to 100 (white)
a*: from 100 (red) to −100 (green)
b*: from 100 (yellow) to −100 (blue)

For the lightening effects, L* and b* are combined to calculate the ITA parameter (Individual Typology Angle) using the following formula: ITA°=Arctg $[(L*-50)/b*] \times (180/pi)$.

An increase in L* and ITA° is therefore expected.

In this study, 5 acquisitions were performed at each site with a nozzle of 3 mm diameter.

Results

TABLE 19

Variation of the ITA parameter after 3 weeks of application of the cream according to the invention (N = 25 volunteers, n = 5 measures/site)

| | Hyperpigmented site | | | | Control site | |
| --- | --- | --- | --- | --- | --- | --- |
| | Cream of the invention | | Placebo | | Non treated | |
| | T0 | T21 | T0 | T21 | T0 | T21 |
| Mean | 17.48 | 20.61 | 18.76 | 20.04 | 18.04 | 18.30 |
| Standard deviation | 7.71 | 8.09 | 7.33 | 6.13 | 9.57 | 9.60 |

TABLE 19-continued

Variation of the ITA parameter after 3 weeks of application of the cream according to the invention (N = 25 volunteers, n = 5 measures/site)

| | Hyperpigmented site | | | | Control site | |
| --- | --- | --- | --- | --- | --- | --- |
| | Cream of the invention | | Placebo | | Non treated | |
| | T0 | T21 | T0 | T21 | T0 | T21 |
| % variation vs. T0 | | 17.9% | | 6.8% | | 1.5% |
| Corrected % variation of the control site | | 16.5% | | 5.4% | | |
| Significance vs. T0 | | p < 0.0188% | | nsd | | |
| Responders Significance vs. Placebo | | p < 0.05 | | | | |

The analysis of the results shows a lightening of the hyperpigmented site after only 3 weeks of application of the cream of the invention: an increase of the ITA of 16.5% (p<0.01) is observed while at the same time the application of a placebo causes a low non-significant variation of 5.4%. The difference between the two treatments is significant at p<0.05.

TABLE 20

Variation of the L* parameter after 3 weeks of application of the cream according to the invention (N = 25 volunteers, n = 5 measures/site)

| | Hyperpigmented site | | | | Control site | |
| --- | --- | --- | --- | --- | --- | --- |
| | Cream of the invention | | Placebo | | Non treated | |
| | T0 | T21 | T0 | T21 | T0 | T21 |
| Mean | 56.15 | 57.41 | 56.47 | 57.23 | 55.91 | 56.13 |
| Standard deviation | 2.67 | 2.80 | 2.56 | 2.38 | 3.05 | 3.06 |
| % variation vs. T0 | | 2.2% | | 1.4% | | 0.4% |
| Corrected % variation of the control site | | 1.9% | | 1% | | |
| Significance vs. T0 | | p < 0.0196% | | p < 0.0568% | | |
| Responders Significance vs. Placebo | | p < 0.05 | | | | |

As for the ITA parameter, the clarity L* is increased significantly after applying the cream according to the invention for 3 weeks. A lightening of the hyperpigmented area was observed of 1.9% (p<0.01), while at the same time applying a placebo causes a smaller change of 1% (p<0.05). The difference between the two treatments is significant at p<0.05.

The invention claimed is:

1. A cosmetic or dermatological active ingredient comprising a mixture of unsaturated dicarboxylic acids comprising Z and E isomers of at least one monounsaturated dicarboxylic C12-C24 acid, the concentration of E-isomer being at least 25% by weight based on the total weight of Z and E isomers.

2. The cosmetic or dermatological active ingredient according to claim 1, wherein the weight ratio of E/Z isomers is from 0.5 to 10:1 based on the total weight of Z and E isomers.

3. The cosmetic or dermatological active ingredient according to claim 1, wherein the mixture comprises at least 80 wt % of said at least one monounsaturated dicarboxylic C12-C24 acid and/or less than 20% by weight of at least one di-unsaturated and/or tri-unsaturated C12-C24 dicarboxylic acid, based on the total weight of unsaturated dicarboxylic acids.

4. The cosmetic or dermatological active ingredient according to claim 1, wherein the mixture is substantially free from di-unsaturated and/or tri-unsaturated C12-C24 dicarboxylic acid.

5. The cosmetic or dermatological active ingredient according to claim 1, wherein the mixture of unsaturated dicarboxylic acids has an iodine value of 50 to 120 g/100 g, and/or an acid value of 310 to 380 mg of KOH/g and/or a saponification value of 315 to 380 mg KOH/g.

6. The cosmetic or dermatological active ingredient according to claim 1, wherein the mixture of unsaturated dicarboxylic acids is formed by mixing the E isomers of mono-unsaturated dicarboxylic C12-C24 acid obtained by metathesis with Z isomers mono-unsaturated dicarboxylic C12-C24 acid obtained by fermentation.

7. The cosmetic or dermatological active ingredient according to claim 1, wherein the carbon chain of the at least one monounsaturated dicarboxylic C12-C24 acid comprises 16 to 20 carbon atoms.

8. The cosmetic or dermatological active ingredient according to claim 1, wherein the concentration of E isomer is at least 40% by weight and/or the concentration of Z isomer is at most 60% by weight, based on the total weight of Z and E isomers.

9. The cosmetic or dermatological active ingredient according to claim 1, wherein the position of the double bond of the at least one monounsaturated dicarboxylic C12-C24 acid is at the center of the hydrocarbon chain.

10. The cosmetic or dermatological active ingredient according to claim 1, wherein the at least one monounsaturated dicarboxylic C12-C24 acid is octadec-9-ene-1,18-dicarboxylic acid, $$(HO(O)C(CH_2)_7CH\!\!=\!\!CH(CH_2)_7C(O)OH).$$

11. The cosmetic or dermatological active ingredient according to claim 1, further comprising between 0.001% and 5% by weight of at least one anti-oxidant or radical scavenger, based on the total weight of the cosmetic or dermatological active ingredient.

12. The cosmetic or dermatological active ingredient according to claim 11, wherein the anti-oxidant or radical scavenger is selected from tocopherol, bisabolol, tocopherol acetate, ascorbyl palmitate, butylated hydroxytoluene and pentaerythrityl tetra-di-t-butyl hydroxyhydrocinnamate and mixtures thereof.

13. A cosmetic or dermatological composition comprising an effective amount of the cosmetic or dermatological active ingredient according to claim 1 and a physiologically acceptable excipient.

14. The cosmetic or dermatological composition according to claim 13, further comprising at least one additional active ingredient.

15. The cosmetic or dermatological composition according to claim 14, wherein the at least one additional active ingredient is selected from lightening, pro-pigmenting, anti-redness, anti-spots, calming, sunscreens, moisturizing, humectant, exfoliant, smoothing, toners, anti-aging, anti-wrinkle and fine lines, improving the mechanical and elastic properties, acting on the complexion, detoxifying, anti-hair regrowth, anti-acne, acting on sebum secretion, mattifying, unifying, anti-inflammatories, antioxidants, anti-free radical, anti-glycants, antidandruff, eye contours (dark circles and under-eye bags), promoting blood circulation, peptides and vitamins actives.

16. The cosmetic or dermatological composition according to claim 14, wherein the at least one additional active ingredient is at least one additional lightening active selected from vitamin C and ascorbic acid derivatives, niacinamide, licorice root extract (*Glycyrrhiza glabra* (licorice) root extract) and arbutin.

17. The cosmetic or dermatological composition according to claim 13, wherein the cosmetic or dermatological active ingredient is in a bound, incorporated or adsorbed form on macro-, micro-, and nanoparticles, or macro-, micro- and nanocapsules, for the treatment of textiles, natural or synthetic fibers, wool and materials intended to come into contact with the skin and can be used in clothing, day or night underwear, handkerchiefs or tissues, in order to exercise cosmetic or dermatological effect through the skin/textile contact and permit continuous topical delivery.

18. A method of treating skin or appendages comprising applying to the skin or appendages a cosmetic or dermatological active composition according to claim 13.

19. The method according to claim 18, wherein the treatment is a dermatological treatment selected from topical anti-bacterial treatment, anti-microbial, anti-inflammatory, anti-acne, against pimples, rosacea, lentigo, and dermatosis.

20. The method according to claim 18, wherein the cosmetic or dermatological active ingredient is present at a concentration of 0.01% to 20% by weight relative to the total composition weight.

21. The method according to claim 18, wherein the treatment is a topical treatment.

22. The method according to claim 21, wherein the topical treatment is selected from the following treatments:
To reduce the production of melanin in the skin,
To lighten the skin and its appendages,
To attenuate skin spots,
To homogenize skin color,
To hydrate,
To fight against dry skin,
To protect and/or reinforce the skin barrier,
For stimulating the synthesis of at least one of the molecules of the dermal extracellular matrix,
Antioxidant
Anti-wrinkles and fine lines,
Slimming,
To improve the mechanical properties of the skin firmness and/or elasticity and/or flexibility and/or suppleness,
Lipofiling promoting the expansion and/or the formation of subcutaneous adipose tissue in order to improve and/or embellish any part of the body having a deficit in lipids,
Anti-aging,
Oily skin,
Acne prone skin,
Anti-dandruff,
Acting on hair and nails growth,
Peeling,
Against solar radiations,
Deodorant,
Anti-seborrheic,
Antiglycation,
Promoting re-epithelialization and/or regeneration of the skin or the lips and the contour of the hair root or nails, and
To improve skin comfort affected by cold, UV or mechanical frictions.

23. The method according to claim 18, wherein the treatment is for treating skin of V and/or VI phenotypes.

24. Mixture of unsaturated dicarboxylic acids comprising Z and E isomers of at least one monounsaturated C12-C24 dicarboxylic acid, wherein the concentration of (i) E isomer is at least 40% by weight and Z isomer is at most 60% by weight both based on the total weight of Z and E isomers, (ii) saturated dicarboxylic acid is 0.1% to 4% by weight based on the total weight of the mixture, and (iii) monocarboxylic acid is 0.15 to 0.5% by weight based on the total weight of the mixture.

25. Mixture according to claim 24, wherein the mixture has at least one of the following values: (i) iodine value of 50 to 120 g/100 g (ii) acid value from 310 to 380 KOH mg/g, and (iii) saponification value from 315 to 380 KOH mg/g.

26. The cosmetic or dermatological composition according to claim 16, wherein the at least one additional active ingredient is an ascorbic acid derivative selected from ethyl ascorbic acid, ascorbyl glucoside, magnesium ascorbyl phosphate, sodium ascorbyl phosphate, disodium ascorbyl sulfate, and ascorbyl tetraisopalmitate.

27. The method according to claim 19, wherein the treatment is dermatosis selected from hyperpigmentary, eczema, and impetigo.

* * * * *